United States Patent [19]
White

[11] Patent Number: 5,984,675
[45] Date of Patent: Nov. 16, 1999

[54] INTERACTIVE ORTHODONTIC SPRING SYSTEM

[75] Inventor: Velton Curtis White, W. 590 Kearney Rd., Burlington, Wis. 53105

[73] Assignee: Velton Curtis White, Burlington, Wis.

[21] Appl. No.: 08/848,983

[22] Filed: May 2, 1997

[51] Int. Cl.$^6$ .................................................. A61C 3/00
[52] U.S. Cl. .............................................. 433/21; 433/24
[58] Field of Search ................................ 433/18, 21, 24, 433/8

[56] References Cited

U.S. PATENT DOCUMENTS

| | | | |
|---|---|---|---|
| 3,256,602 | 6/1966 | Broussard et al. | 433/21 X |
| 4,354,834 | 10/1982 | Wilson | 433/21 |
| 4,976,614 | 12/1990 | Tepper | 433/21 X |
| 5,246,366 | 9/1993 | Tracey | 433/21 |

Primary Examiner—Nicholas D. Lucchesi
Attorney, Agent, or Firm—Holme Roberts & Owen LLP

[57] ABSTRACT

An orthodontic spring system is provided for primary intended use with conventional fixed appliance systems. The orthodontic spring system includes one or more orthodontic spring devices that may actively grip a fixed orthodontic appliance during use for enhanced delivery of aligning forces and tooth/root control. The orthodontic spring devices may include two or more spring segments for applying tooth aligning forces in transverse directions. Additionally, the orthodontic springs may include one or more bends to provide for deflection of adjacent springs portions, twisting, wherein the orthodontic spring devices may be used to apply alignment forces in three different planes. The orthodontic springs are provided such that, when the maloccluded teeth to be repositioned have assumed their desired position, the interconnected springs will assume a substantially inactive state. Use of the inventive system provides for rapid, biomechanically induced tooth rotation, tooth inclination, tooth intrusion/extrusion and tooth axis movement as may be desired for a given situation.

40 Claims, 16 Drawing Sheets

MANDIBULAR

MAXILLARY

MANDIBULAR

INTERACTIVE ORTHODONTIC SPRING SYSTEM

FIELD OF THE INVENTION

The present invention pertains to orthodontic springs and more particularly, to orthodontic springs for use with conventional fixed orthodontic appliance systems to interactively achieve rapid, biomechanically-induced tooth movement. The springs provide for a relatively wide range of activation, moderate force application rates, enhanced tooth control, tri-planar force application and are readily attachable to conventional fixed appliances.

BACKGROUND OF THE INVENTION

Developments in the field of orthodontics continue to provide orthodontists with an ever-increasing number of competing options to address patient needs. In turn, such competing options have resulted in varying expectations and treatment plans.

Despite such variations, however, competing fixed orthodontia options continue to have many similarities. That is, conventional fixed orthodontic systems all utilize brackets, buccal tubes or similar fixed appliances secured to individual teeth and an arch wire passing therebetween, most commonly through bracket slots and/or ligated to the bracket tie wing(s). In some instances, the arch wire is preformed and/or additional accessories are interconnected to the brackets to apply the desired alignment forces. In the case of edgewise brackets, significant advances have been made in relation to angulation of the mesial-distal arch wire slot for purposes of more effectively "tipping" the root of a tooth to correct crown angle and more effectively applying torque to address inclination objectives.

It has been recognized, however, that slot-oriented approaches can provide only a marginal degree of control over the movement of the root of a tooth and are otherwise unable to realize optimal lingual-buccal tooth positioning. Additionally, slot-oriented approaches yield a range of achievable tipping, spreading and eruption/intrusion that may be insufficient to address severely malposed teeth. Consequently, such approaches can result in stop-go treatment progress, which can delay and otherwise impede the overall efficacy of treatment.

SUMMARY OF THE INVENTION

In view of the foregoing, a primary objective of the present invention is to provide an orthodontic spring system for use with conventional fixed orthodontia to reduce overall treatment time via rapid initial tooth positioning. In turn, such rapid positioning enhances the opportunity to successfully treat severely malposed teeth before a determination regarding extraction need be made. A closely related objective is to reduce the incidence of tooth extractions, thereby increasing efficiencies and reducing patient anguish and discomfort.

A further objective of the present invention is to provide an improved orthodontic spring system which achieves rapid tooth movement with reduced patient discomfort and impact on the supporting tissue of the roots of the aligned teeth.

Yet another objective of the present invention is to provide an improved orthodontic spring system for achieving enhanced tooth/root control and tooth/root movement, and which can be readily applied by orthodontists.

To realize one or more of the foregoing objectives, the inventive orthodontic spring system recognizes that a separate orthodontic spring device(s) that can be employed with a conventional fixed appliance system on selected teeth to effect controlled tooth movement in up to three different planes are most effective in achieving the desired results. Relatedly, the present invention recognizes that orthodontic spring device(s) which can actively grip fixed appliances and thereby control the corresponding tooth/root can dramatically facilitate positive results. Of further importance, the present invention recognizes that an orthodontic spring system having the noted attributes can be utilized with conventional fixed appliance systems in a manner that provides for enhanced interaction between the system components and a plurality of adjacent teeth to address the desired positioning objectives.

For purposes hereof, the term "fixed orthodontic appliance system" means one in which a separate appliance is bonded or banded to each of a plurality of teeth (e.g. within the maxillary jaw or mandibular jaw), and wherein the orthodontic appliances are interconnected to an orthodontic archwire passing therebetween (e.g. via a ligating device). Most typically, such orthodontic appliances are brackets, such as edgewise brackets, having a mesial-distal slot for receiving the archwire, and one or more tie wings extending gingivally and/or occlusally for ligating the bracket to the archwire.

In one aspect of the invention an orthodontic spring device is provided for selective interconnection to and gripping of a fixed orthodontic appliance at one or both ends. The spring device may be advantageously formed from a single length of wire (e.g. via cold-work bending followed by heat treatment for stress relief/precipitation) to include two integral U-shaped attachment ends. In a passive or inactive state the two U-shaped attachment ends may each extend laterally (e.g. mesially-distally) and may be centered upon a common central axis or parallel axes to facilitate design, use and manufacture. Each U-shaped attachment end may comprise a first spring leg and a second spring leg disposed in opposing relation to the first spring leg, wherein each U-shaped end is spring-loaded to actively grip a portion of a fixed orthodontic appliance. Such gripping action provides for enhanced delivery of tooth positioning forces and enhanced tooth/root control during use. In this regard, the first and second spring legs may be spaced by at least a first distance which is less than a width of that portion of the fixed appliance to be gripped therebetween. By way of example, the first and second spring legs may engage the gingivally and occlusally disposed surfaces of an edgewise bracket for enhanced application of forces for intrusion/extrusion, rotation and inclination. Further a back portion of each U-shaped member, which adjoins the first and second spring legs, may advantageously contact a mesial or distal facing surface of a fixed appliance to pull together/spread teeth or to tip teeth as may be desired. By virtue of the enhanced delivery of tooth aligning forces through the gripping attachment ends of the present invention, it should be appreciated that enhanced tooth positioning, via biomechanically induced root movement, can be achieved. In turn, by moving the roots of teeth, enhanced interaction between adjacent teeth interconnected to a conventional fixed appliance system can be realized, thereby resulting in teeth whose roots are also aligned in a more parallel orientation. Such a result provides for enhanced long term maintenance of the aligned teeth.

In a related aspect of the invention, an orthodontic spring device is provided which includes at least one spring segment activatable to apply a first tooth positioning force in a first direction, and at least one spring segment activatable to apply a tooth positioning force in a second direction, said first and second directions being transverse (e.g. gingivally/ occlusally vs. mesially/distally). Preferably, each of the spring segments exhibits a substantially linear spring rate across a relatively wide range of activation, wherein the total force applied to a tooth in a given plane can be maintained within an appropriate range conducive for rapid yet biophysically acceptable response. The first and second spring segments may each be of a U-shaped configuration, and may include one or more helical loops to increase the range of achievable deflection and activation while maintaining a spring rate within an acceptable range. To provide for transverse force vectors, and by way of example, a center axis for a first U-shaped spring segment in an inactive state may be disposed substantially perpendicular to a center axis of a second U-shaped spring segment in an inactive state. As will be further discussed, the spring segments can be activated, inter alia, to spread apart/pull together maloccluded teeth and/or to intrude/extrude maloccluded teeth. Further, via interaction with the conventional fixed appliance system, the spring segments can also indirectly yield anterior/posterior force application.

In a further related aspect of the invention, an orthodontic spring device is provided which preferably lies substantially in a single plane in an inactive state, and which can be activated to twist, or deflect, about one or more bends provided in the spring, wherein adjacent portions of the spring device can be positioned in adjoining transverse planes. More particularly, by virtue of such out-of-plane deflection upon installation, the orthodontic spring will be activated to directly apply inward/outward tooth positioning forces for inter alia, torquing, anterior/posterior tooth/root movement and tooth inclination. By way of example only, each bend may be readily defined by a 90° turn in a formed wire, a smooth 180° turn at the base of a U-shaped segment, or a helical loop may be employed to define the bend in order to increase the range of achievable anterior/posterior deflection, while maintaining the spring rate within an acceptable range. In this regard, the inventive orthodontic spring may further include an intermediate segment having a helical loop at each of two more corners, wherein a tie-in wire segment is defined between two-helical loops. Such tie-in wire segment may be oriented to extend substantially parallel or coaxially with the center axis of one or both the above-described U-shaped attachment ends. In use, the tie-segment can be employed for interconnection (e.g. via a ligating device) with a fixed appliance on a tooth to be positioned between the two teeth to which the ends of the orthodontic device are mounted.

An orthodontic spring device which provides for the noted biplanar twisting, and which also includes at least two U-shaped spring segments, can provide for the application of tooth positioning forces in three different planes. Further, by utilizing the U-shaped gripping attachment ends described above, the orthodontic spring device can not only achieve enhanced application of forces and tooth control, but may also provide for more effective rotation of the teeth to which the U-shaped attachment ends are interconnected. To best facilitate such rotation, the U-shaped attachment end may twist, or rotate, relative to the rest of the orthodontic spring device about a bend (e.g. 90°) adjoining the attachment end to the balance of the spring device. Such bend may also facilitate mesial/distal rotation of the attachment end for interconnection to a bracket mounted on a tooth to be substantially tipped (e.g. 90°).

In another aspect of the present invention, a method is provided for augmenting the positioning of one or more maloccluded teeth, relative to a plurality of teeth, such plurality of teeth each having a fixed orthodontic appliance interconnected thereto and being interconnected to an orthodontic arch wire. The method includes the interconnection of one end of an orthodontic spring to a first orthodontic appliance interconnected to one of the plurality of teeth, and interconnection of another end of the orthodontic spring to a second orthodontic appliance interconnected to another of said plurality of teeth. Contemporaneous with such interconnection, the orthodontic spring is activated to apply a tooth positioning force to at least one of the orthodontic appliances in at least a first plane. Such force is applied to move one or more of the maloccluded teeth to a desired position, wherein in the desired position the orthodontic spring is designed to automatically assume a substantially inactive or passive state. For purposes hereof, in such inactive or passive state the orthodontic spring will not exert a force sufficient to overcome the resistance of a given tooth and the interconnected appliance/archwire system to effect further movement (e.g., the force will be less than about 20 gms./mm., and most likely less than about 10 gms./mm.). In this regard, the spring may be provided to lie substantially in a single plane in its totally inactive state. As will be appreciated, the invention may further include activating a plurality of spring segments in an orthodontic spring to apply force(s) to maloccluded teeth in up to three different planes of operation, wherein when the maloccluded teeth have reached the desired position all spring segments of the spring will automatically assume a substantially inactive state (e.g. wherein they are unable to effect further movement). Preferably, upon activation the spring segments will provide for a substantially linear and predetermined spring force delivery rate in each plane of activation, wherein rapid, biophysically sound and relatively steady root/tooth positioning can be realized.

The inventive method may be employed by interconnecting opposing ends of the orthodontic spring to adjacent teeth, or interconnecting such ends to two teeth which will be separated by another intermediate tooth positioned therebetween upon the achievement of the desired tooth positioning. In the latter regard, the method may further include interconnecting (e.g. via ligation) an intermediate spring segment of the spring device to the intermediate tooth, and using the intermediate spring segment to apply a positioning force (e.g. gingivally/occlusally and/or anteriorly/ posteriorly) to yield the desired movement of the intermediate tooth. In such applications the appliance on the intermediate tooth may not initially be interconnected (e.g. via ligation or otherwise) to the archwire of the conventional fixed appliance system. As such, the method may further include utilizing the orthodontic spring to move the intermediate tooth to an intermediate position, interconnecting the appliance on the intermediate tooth to the archwire (e.g. via ligation), then continuing to use the orthodontic spring to induce movement of the intermediate tooth to the desired position.

In a further related aspect of the inventive method, the interconnection of one or both ends of the orthodontic spring may include the gripping of a portion of an orthodontic appliance, e.g. between spring-loaded, opposing leg(s) of a U-shaped attachment end. In this regard, where the orthodontic appliance is of a type which includes one or more tie wings, (e.g. a standard edgewise bracket) the application of tooth positioning forces in the inventive method may be further enhanced by engaging an attachment end of the orthodontic spring with the lingual-facing side of a tie wing to effect rapid and controlled tooth rotation. Relatedly, the use of a gripping attachment end as described above, will serve to enhance the delivery of forces and control over tooth movement. As a result, the inventive method may advantageously realize enhanced parallel positioning of the roots of teeth interconnected in a conventional fixed appliance system.

While not wishing to limit the scope or application of the present invention, the disclosed orthodontic spring device and method are primarily intended to augment conventional fixed appliance system(s), wherein tooth positioning is achievable in a rapid and medically sound manner. In this regard, it will be understood that forces applied to a given tooth via the inventive spring and method may serve to not only induce movement of that tooth but additionally be communicated to induce movement (e.g. mesially/distally to adjacent teeth via direct tooth/root contact and/or via the archwire of the conventional fixed appliance system. Relatedly, it will be understood that the presence of the conventional fixed appliance system can serve to define anchor positions of teeth, thereby allowing the applied spring forces to be directed and communicated to the desired teeth in a predetermined manner so as to induce the intended tooth movement.

As noted, such tooth positioning may be achieved with enhanced tooth/root control in three different planes of operation. As a result, the present invention may be utilized to achieve intrusion/extrusion, spreading/pulling together, tipping, torquing, toothlong axis translation and rotation at a rate not heretofore realizable. Such rapid positioning will reduce overall treatment time, reduce tooth extraction situations and enhance patient satisfaction. Numerous additional inventive features and associated advantages will become apparent upon consideration of the detailed description which follows.

DETAILED DESCRIPTION

FIGS. 1A–1F illustrate one embodiment of an orthodontic spring system comprising the present invention. More particularly, FIGS. 1A–1F illustrate six different orthodontic spring devices, each of which includes one or more inventive aspects.

The devices illustrated in FIGS. 1A–1F each generally comprise a length of wire that has been bent into a specific desired shape e.g. to yield a plurality of desired spring segments for applying tooth alignment forces upon installation/activation. Each of the spring segments of the various devices are illustrated in an inactive state, including their respective end attachment(s) $10a–10f$ for interconnection to fixed orthodontic appliances.

More particularly, each of the spring devices illustrated in FIGS. 1A–1F utilize an end attachment $10a–10f$ for interconnection with a fixed orthodontic bracket, buccal tube or the like attached to a tooth. Each end attachment $10a–10f$ is generally U-shaped with two opposing spring legs $12a–12f$ and $14a–14f$ that are connected via 90° bent comers $16a–16f$ to a back leg $18a–18f$. The spring legs $12a–12f$ and $14a–14f$ each comprise a teardrop-shaped wire loop thereby combinatively defining a key-hole shaped opening $20a–20f$ therebetween for receiving a fixed orthodontic appliance. The wire loop spring legs $12a–12f$, $14a–14f$, together with the 90° bent comers $16a–16f$ provide predeterminable spring-loading for compressive engagement with a fixed orthodontic appliance therebetween, e.g. occlusally-facing and gingivally-facing sides of an edgewise bracket, thereby yielding enhanced force application to and enhanced control over the responsive movement of the corresponding teeth. The rounded ends $22a–22f$ of each spring leg $14a–14f$ and $16a–16f$ allow the end attachments $10a–10f$ to be progressively advanced (e.g. mesially or distally) on a bracket or the like, whereupon the opposing spring legs $12a–12f$ and $14a–14f$ effectively capture and grip the bracket within the key-hole shaped opening $20a–20f$. While shown facing outward in FIGS. 1A–1F, it is noted that end attachments $10a–10f$ may be disposed inwardly (e.g., rotated 180° relative to orientation shown) upon initial formation.

Figure 1A:
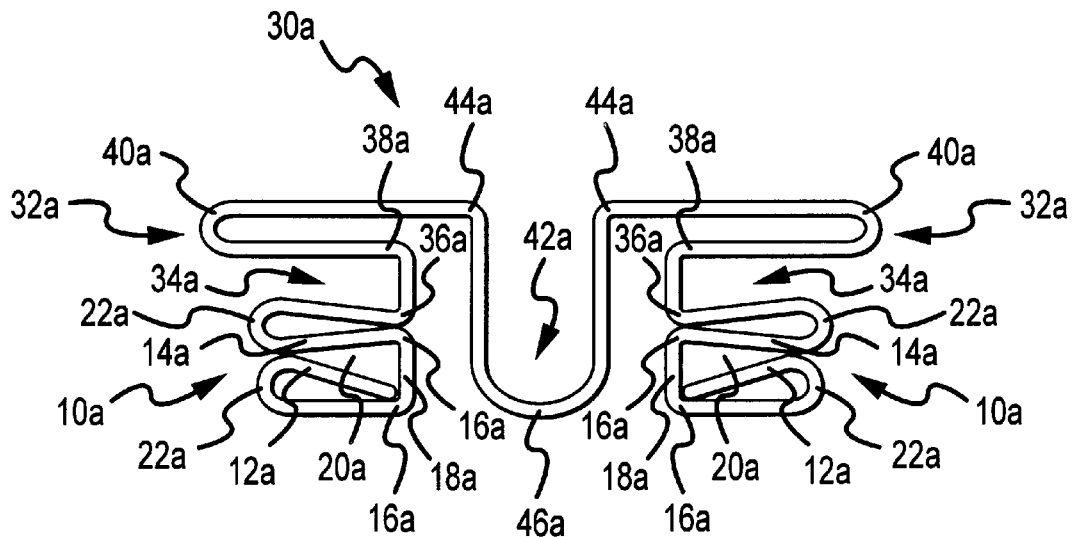
FIGS. 1A–1F illustrate various orthodontic spring devices comprising one embodiment of the present invention.
Figure 1B:
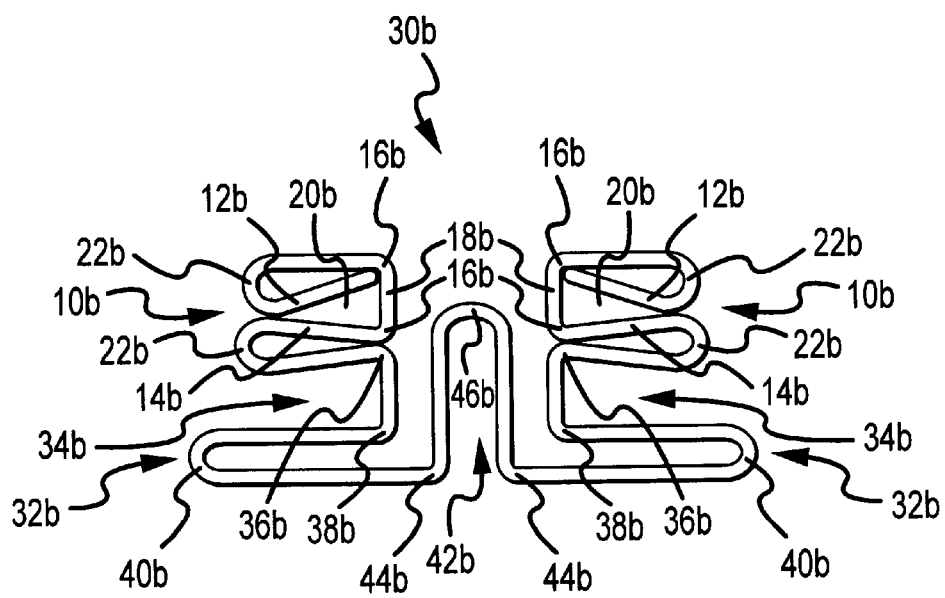

With specific reference to FIGS. 1A and 1B, the illustrated orthodontic springs $30a–30b$ are intended for use on two adjacent teeth in the upper (i.e. maxillary) and lower (i.e. mandibular) jaws, respectively. By way of primary example, springs $30a$ and $30b$ and may be interconnected to adjacent upper central teeth and adjacent lower central teeth, respectively.

The springs $30a$, $30b$ include a laterally-extending mesial and distal foot spring segment(s) $32a$, $32b$ of an inwardly-facing, U-shaped configuration, with corresponding outwardly-facing mesial and distal U-shaped intermediate spring segment(s) $34a$, $34b$ interposed therebetween. Each intermediate spring segment $34a$, $34b$ is defined by two 90° bends $36a$ and $38a$, $36b$ and $38b$, while each foot spring segment $32a$, $32b$ is defined by a continuous 180° bend $40a$, $40b$. As illustrated, each spring $30a$, $30b$ further includes a single gingivally-extending, U-shaped central spring segment $42a$, $42b$, adjoined at its ends to mesial and distal foot spring segment(s) $32a$, $32b$ via 90° bends $44a$, $44b$. Each central spring segment $42a$, $42b$ is defined by a continuous 180° bend $46a$, $46b$. As will be appreciated, in addition to providing alignment forces, central spring segments $42a$, $42b$ are also disposed for comfortably receiving the upper and lower central frenum tissue during use.

The spring segments $32a$, $32b$, $34a$, $34b$, and $42a$, $42b$, and the numerous bends of the described springs $30a$, $30b$, can be utilized to apply alignment forces to teeth in three different planes. More particularly, spring segments $32a$, $32b$ and $34a$, $34b$ can be activated (e.g. expanded or compressed) to directly apply gingivally-occlusally directed forces for tooth intrusion/extrusion, and spring segment $42$, $42b$ can be activated to directly apply mesially-distally directed forces for spreading/pulling together teeth. The bends (e.g. both 90° and 180°) can be activated to deflect adjacent portions of the springs $30a$, $30b$ into transverse planes and thereby apply anterior/posterior directed forces for torquing, inclining/declining and anterior/posterior tooth positioning. Attachment ends $10a$, $10b$ can be activated via rotation at bend $36a$, $36b$ (e.g., up to about ±90°) for rotating the interconnected teeth in a controlled manner.

Figure 1C:
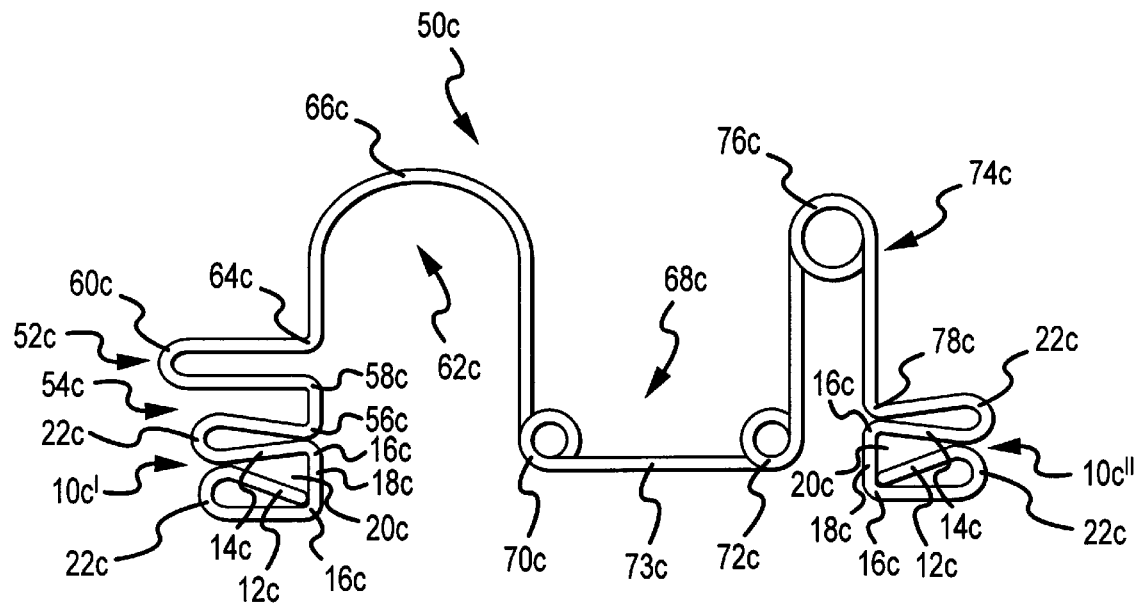
Figure 1D:
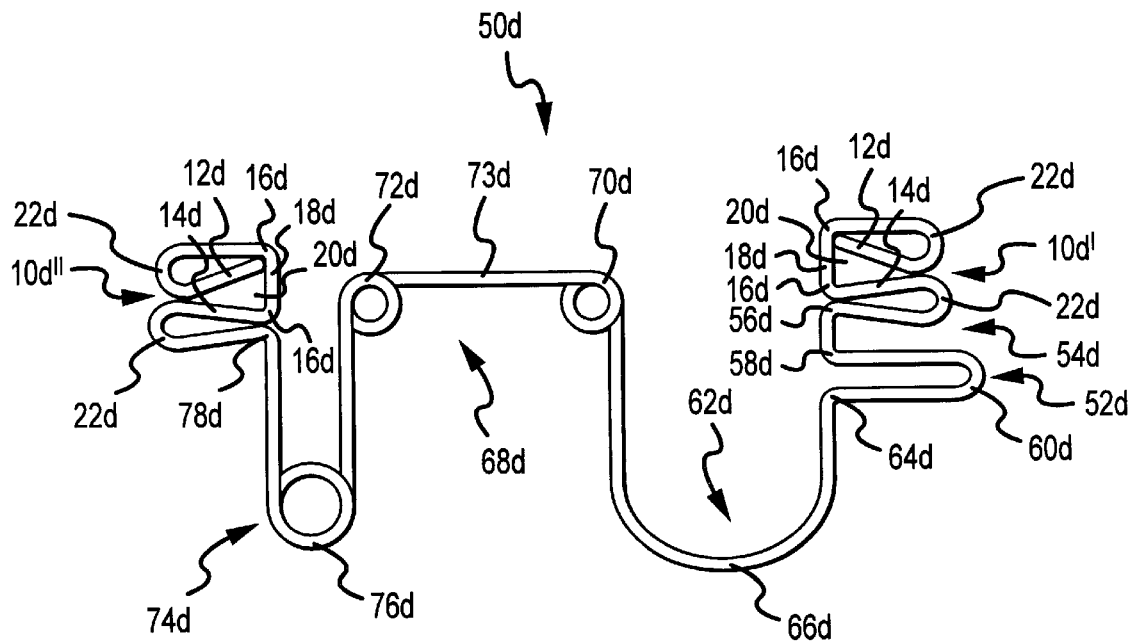

FIGS. 1C and 1D illustrate springs $50c$ and $50d$ which are intended to interface with three adjacent teeth in the upper (i.e. maxillary) jaw and lower (i.e., mandibular) jaw, respectively. In this regard, the orthodontic springs 50c and 50d, as illustrated in FIGS. 1C and 1D, are oriented for use in the upper right quadrant and lower left quadrant, respectively. For use in the upper left quadrant, spring device 50c would be rotated 180° about a vertical axis. Similarly, for use in the lower right quadrant, spring device 50d would be rotated 180° about a vertical axis. By way of primary example, springs 50c, 50d may be interconnected via their respective distal and mesial attachment ends 10c' and 10c'', 10d' and 10d,'' to fixed orthodontic appliances on the central and cuspid teeth in any quadrant, and can actively engage, for example, a fixed appliance on a maloccluded lateral to be positioned between such lateral and bicuspid teeth via ligation. In this regard, springs 50c, 50d can serve to rapidly spread corresponding central and cuspid teeth and advance/retract the corresponding maloccluded lateral therebetween.

In the orthodontic springs 50c, 50d, distally extending attachment end 10c', 10d' is interconnected to a gingivally offset, laterally extending (i.e. mesially-distally) foot spring segment 52c, 52d of an inwardly facing, U-shaped configuration with an outwardly-facing U-shaped intermediate spring segment 54c, 54d therebetween. The intermediate spring segment 54c, 54d is defined by two 90° bends 56c and 56d, 58c and 58d, while foot spring segment 54c, 54d is defined by a continuous 180° bend 60c, 60d. The foot spring segment 52c, 52d is interconnected to a gingivally-extending, U-shaped first offset spring segment 62c, 62d via a 90° bend 64c, 64d. The first offset spring segment 64c, 64d is defined by a continuous 180° bend 66c, 66d and adjoins an occlusally-extending central spring segment 68c, 68d of U-shaped configuration. The central spring segment 68c, 68d comprises a first 450° helical loop 70c, 70d and second 450° helical loop 72c, 72d. Central spring segment 68c, 68d is adjoined to a gingivally-extending, U-shaped second offset spring segment 74c, 74d, which comprises a continuous 540° helical loop 76c, 76d. The second offset spring segment 74c, 74d is interconnected to the mesially positioned attachment end 10c'', 10d'' via 90° bend 78c, 78d.

As will be appreciated, spring segments 52c, 52d, and 54c, 54d, and 62c, 62d, and 68c, 68d, and 74c, 74d, and the numerous bends of springs 50c, 50d can be utilized to apply alignment forces to teeth in three different planes. More particularly, spring segments 52c, 52d, and 54c, 54d can be activated (e.g. expanded or compressed) to directly apply gingivally-occlusally directed forces for tooth intrusion/extrusion. Spring segments 62c, 62d, and 68c 68d, and 74c, 74d can be activated to directly apply mesially/distally directed forces for spreading/pulling together teeth. In this regard, it is noted that the helical loops 70c, 70d and 72c, 72d, and 76c, 76d can serve to increase the mesial/distal range of activation when maintaining spring rates within a biophysically appropriate range. The bends (e.g. both 90° 180°) and can be activated to deflect adjacent portions within springs 50c, 50d into transverse planes and thereby apply anterior/posterior directed forces for torquing, and inclining/declining teeth, as well as anterior/posterior tooth positioning. Helical loops 70c, 70d, and 72c, 72d, and 76c, 76d will advantageously increase the range of anterior/posterior spring deflection while maintaining spring rates within acceptable ranges for sound biophysical root/tooth movement. Attachment ends 10c',10d' and 10c, 10d'' can be activated via rotation at bends 56c, 56d and 78c, 78d (e.g., up to about ±90°) for rotating the interconnected teeth in a controlled manner.

Figure 1E:
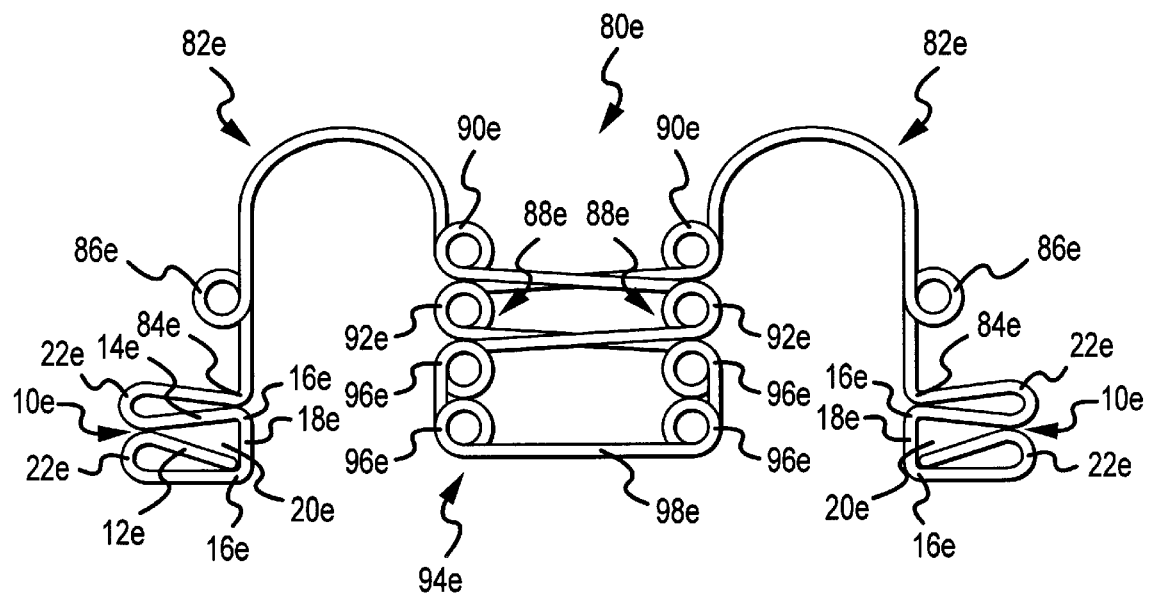

FIG. 1E illustrates another orthodontic spring 80e intended for use with three adjacent teeth in the upper (i.e. maxillary) jaw. For use in the lower mandibular jaw, the spring 80e would simply need to be rotated 180° (i.e. about a horizontal axis) into a downward orientation. By way of primary example, the two attachment ends 10e of spring 80e may be interconnected to fixed appliances on the cuspid and second bicuspid teeth in a given quadrant, with an appliance on the first bicuspid therebetween being selectively attachable, e.g. via ligation, as will be further described.

The orthodontic spring 80e comprises a gingivally extending, U-shaped offset spring segment 82e adjoined to each attachment end 10e with a 90° bend 84e therebetween. An intermediate 360° helical loop 86e is included in each offset spring segment 82e. The two offset spring segments 82e are each interconnected to corresponding laterally-extending, U-shaped spring segments 88e via 450° helical loops 90e. The laterally extending spring segments 88e each comprise a 540° helical loop 92e. The two lateral spring segments 88e substantially overlap and are adjoined at their respective ends to a central U-shaped tie-in spring segment 94e. The tie-in spring segment includes 450° helical loops 96e positioned at each of its four corners. The occlusal-facing side 98e of the tie-in spring segment 94e can be utilized for selective interconnection with a bracket on the middle of the three teeth to which spring 80e is applied.

The spring segments 82e, 88e, 94e and numerous bends of spring 80e can be activated to apply alignment forces in three planes. More particularly, spring segments 82e can be utilized if activated (e.g. expanded or compressed) to directly apply mesially/distally directed forces for spreading/pulling teeth together and otherwise tipping teeth. The lateral spring segments 88e can be activated (e.g. expanded or compressed) to apply gingivally/occlusally directed forces for tooth intrusion/extrusion. The bends (e.g. both 90° and 180°) can be activated to deflect adjacent portions of the spring 80e into transverse planes and thereby apply anterior/posterior directive forces, for torquing and inclining/declining teeth and for anterior/posterior tooth/root positioning. In this regard, each of the helical loops 86e, 90e, 92e and 96e provide for an enhanced range of deflection for force application in the three different planes while maintaining spring rates within acceptable biophysical ranges. Attachment ends 10e can be activated via rotation at bend 84e (e.g., up to about ±90°) for rotating the interconnected teeth in a controlled manner.

Figure 1F:
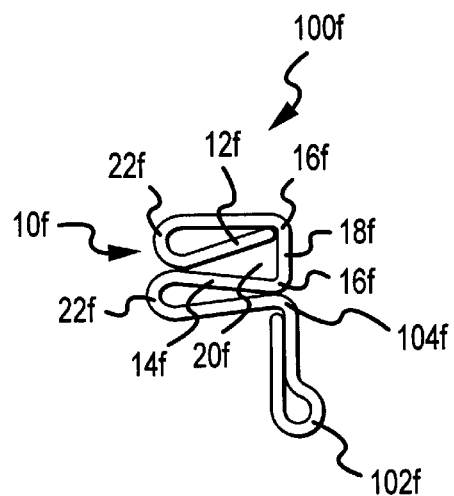

Finally, FIG. 1F illustrates an add-on hook device 100f having an attachment end 10f for attachment to a bracket or the like. As shown, spring hook device 100f includes an occlusally extending loop hook 102f adjoined to attachment end 10f via 90° bend 104f. Hook device 100f may be employed on any tooth, from second bicuspid to second bicuspid, for intraoral and interoral placement of orthodontic elastics. Additionally, hook device 100fcould be employed for post surgical fixation purposes. As can be appreciated, the device 100f can be readily interconnected and removed, thereby reducing the need to solder or weld attachments to a fixation appliance.

Referring now to FIGS. 2A–2F, the various activatable spring features of the orthodontic spring devices of FIG. 1F are illustrated.

Figure 2A:
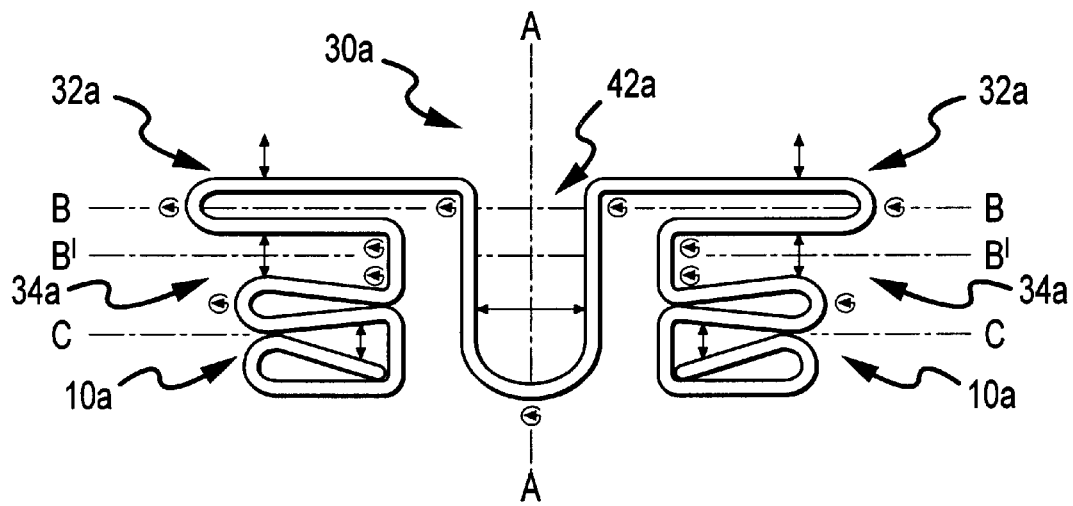
FIGS. 2A–2F illustrate the various activatable spring components of the orthodontic spring devices of FIGS. 1A–1F.
Figure 2B:
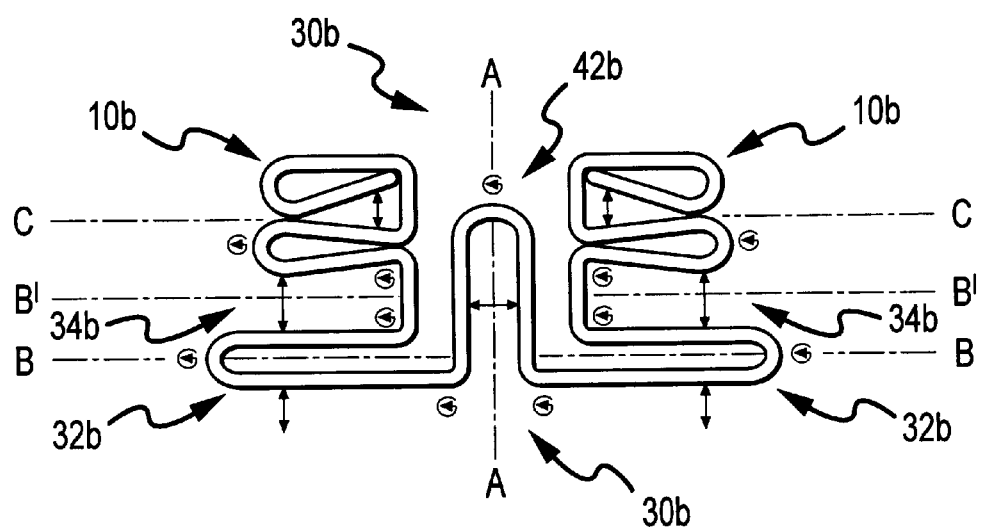

In the orthodontic springs 30a and 30b and as shown in FIGS. 2A and 2B, the attachment ends 10a and 10b are each activatable to grip an orthodontic appliance upon installation, e.g. via the application of a compressive force(s) toward center axis CC of ends 10a, 10b, and to rotate the appliance. Spring Segments 32a, 32b, and 34a, 34b, are activatable to provide gingivally-occlusally directed forces, e.g. toward/away from axis BB and B'B' respectively. Spring segment 42a, 42b is activatable to provide mesially-distally directed alignment force(s), e.g. toward/away from axis AA. It is noted that the center axes BB of spring segments 32a, 32b, and B'B' of spring segments 34a, 34b, are oriented substantially perpendicular to the center axis AA of central spring segment 42a, 42b in the inactive state, as illustrated in FIGS. 2A and 2B. As further illustrated in FIGS. 2A and 2B, springs 30a, 30b each comprise a plurality of bends about which portions of the respective spring devices 30a, 30b may twist, or deflect, during use to provide for the application of inward/outward alignment forces.

Figure 2C:
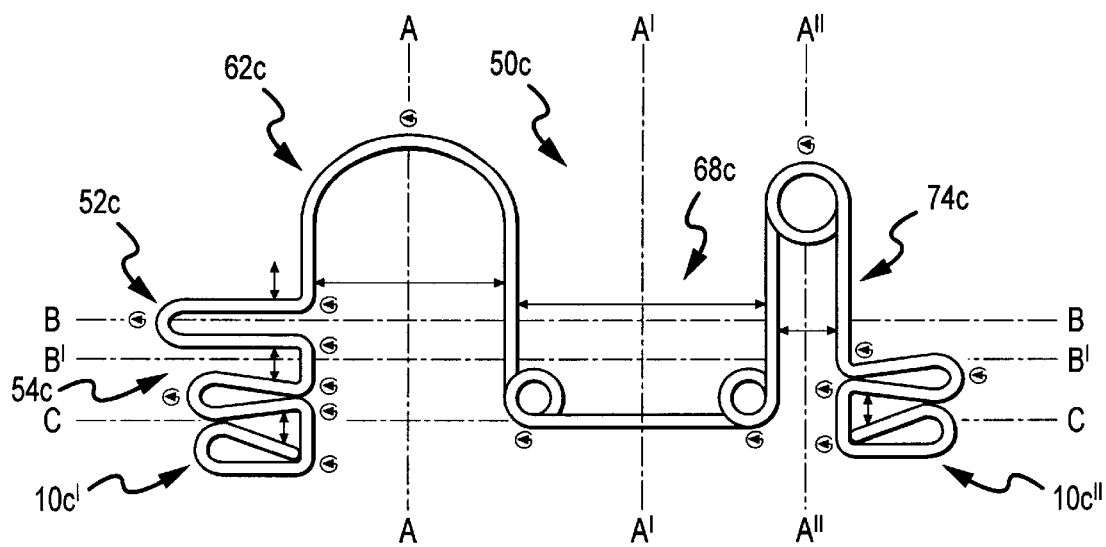
Figure 2D:
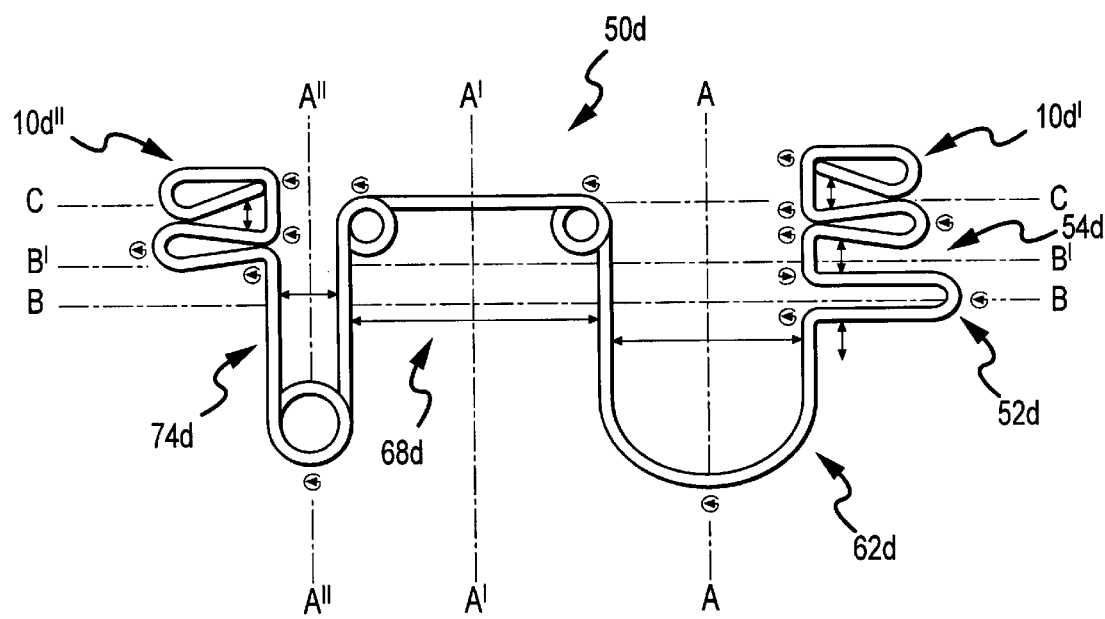

In the orthodontic springs 50c and 50b shown in FIGS. 2C and 2D, the attachment ends 10c' and 10c", and 10d' and 10d" are each activatable upon installation to grip a corresponding orthodontic appliance, e.g. via compressive force application toward axis C, and to rotate the appliance. Additionally, spring segments 52c, 52d, as well as spring segments 54c, 54d, are activatable to provide gingivally-occlusally directed tooth aligning forces, e.g. toward/away from axis BB and B'B', respectively. Spring segments 62c, 62d, spring segments 68c, 68d and spring segments 74c, 74d are each activatable to provide mesially-distally directed tooth alignment forces, e.g. toward/away from axis AA, A'A' and A"A", respectively. In this regard, it is noted that the center axes BB and B'B' are oriented substantially perpendicular to center axes AA, A'A', and A"A" when the spring is in its inactive state. As illustrated, springs 50c and 50d each comprise a plurality of bends about which portions of the respective spring devices 50c, 50d may twist, or deflect, during use to provide for the application of inward/outward alignment forces.

Figure 2E:
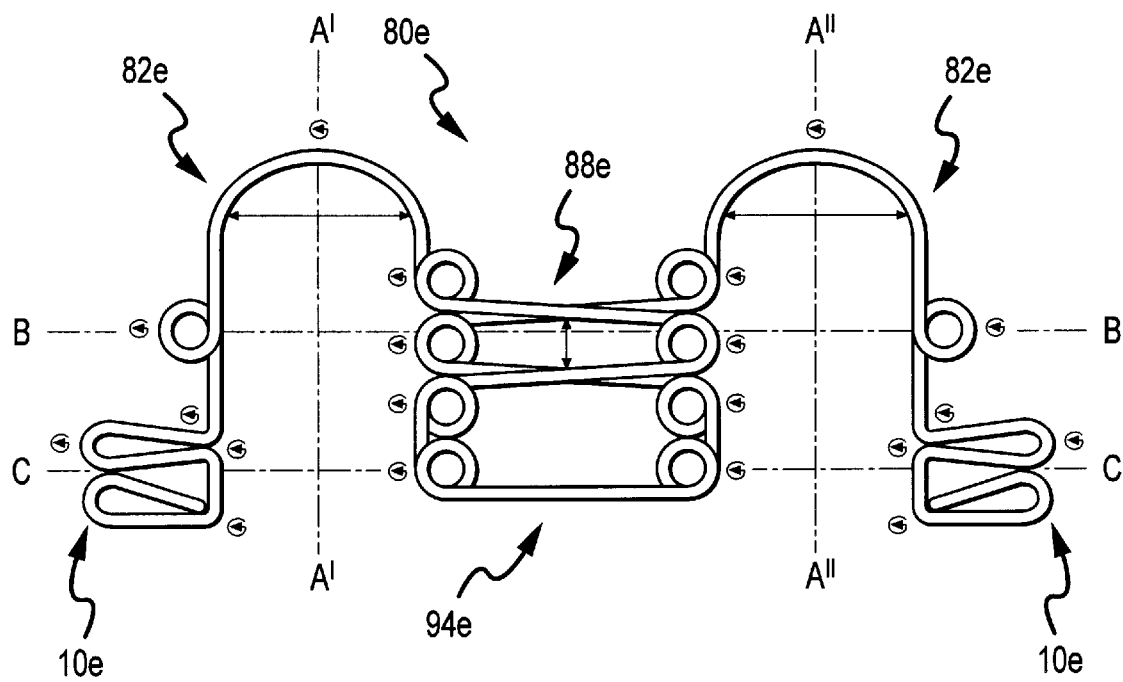

In the orthodontic spring 80e illustrated in FIG. 2e, attachment ends 10e are each activatable to grip a corresponding orthodontic appliance, e.g. via the application of compressive forces toward axis CC, and to rotate the appliance. Spring segments 82e are each activatable to provide mesially-distally directed forces, e.g. toward/away from axes A'A' and A"A". Spring segments 88e are activatable to provide gingivally-occlusally directed aligning forces, e.g. toward/away their common center axis BB. The center axes A'A' and A"A" are each oriented substantially perpendicular to center axes BB and CC. As illustrated, there are a number of bends in spring 80e about which portions of spring device 80e may twist, or deflect to provide for the application of inward/outward aligment forces.

Figure 2F:
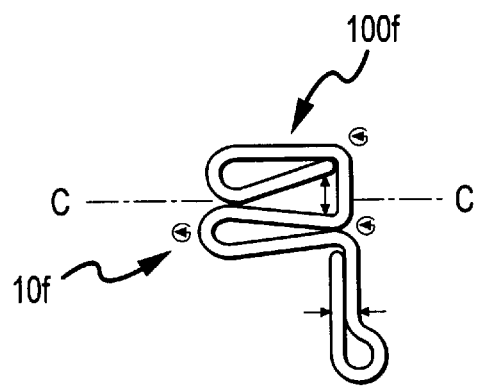

In FIG. 2F, attachment end 10f may grip an orthodontic appliance via the application of compression forces upon installation, e.g. toward axis CC, and can be activated to rotate the appliance. As indicated, there are a number of bends in spring device 100f about which portions of the device may twist, or deflect, to facilitate attachment to accessories and/or for providing anterior-posterior directed alignment forces.

As noted, each of the springs illustrated in 1A–1F, 2A–2F may be formed a single length of wire. More particularly, such wire may be bent, or cold worked into the illustrated configurations, then heat-treated to achieve stress relief and a degree of heat-induced precipitation so as to achieve the desired spring activation and deflection characteristics. By way of example, one wire employable is a chromium cobalt alloy manufactured by Elgiloy Limited. Partnership, located in Elgin, Ill., and marketed in the orthodontic industry under the trademark "ELGILOY" owned by Elgiloy Limited Partnership.

Each of the springs illustrated in FIGS. 1A–1F, 2A–F can be appropriately sized for application of the desired spring forces on a per-patient basis. In this regard, and by way of example, the spring-rates for each of the springs should be provided so that, upon installation of a spring device in a given application, the forces applied to a given tooth are within a range that serve to rapidly move the teeth by overcoming the resistance of the teeth and conventional fixed appliance system components, and yet be low enough to achieve an appropriate biophysical result. In this regard, the following force value ranges have been recognized as optimal for tooth movements:

| Teeth | Short Roots (gm.) | Medium Length Roots (gm.) | Long Roots (gm.) |
| --- | --- | --- | --- |
| Mandibular incisors | 50–55 | 55–65 | 65–70 |
| Mandibular canines | 85–95 | 95–110 | 110–130 |
| Mandibular premolars | 70–80 | 80–90 | 90–100 |
| Maxillary first molars | 280–300 | 300–320 | 320–360 |
| Maxillary incisors | 65–75 | 75–85 | 85–95 |
| Maxillary lateral incisors | 60–65 | 65–70 | 70–80 |
| Maxillary canines | 105–115 | 115–130 | 130–170 |
| Premolars, single roots | 85–100 | 100–115 | 115–135 |
| Premolars, multiroots | 100–110 | 120–130 | 130–140 |
| Mandibular, first molars | 230–250 | 250–270 | 270–320 |

As has been previously noted, the orthodontic spring devices comprising the present invention may be advantageously provided so that, when maloccluded teeth have been repositioned to their desired orientation, the orthodontic spring devices utilized are in a substantially inactive state. In such inactive state the springs will not typically exert a force in any direction which exceeds approximately 20 gms./mm., and even more typically approximately 10 gms./mm. As will be appreciated, such low forces will be generally in sufficient to overcome the resistance of the teeth and archwire to further movement when the maloccluded teeth have been repositioned within a predetermined range of desirable alignment utilizing the present invention.

It is further noted that, in use of each of the orthodontic spring devices 30a, 30b, 50c, 50d and 80e, multiple spring segments of each may be initially activated upon installation and then interact with the conventional fixed appliance system components and teeth to achieve the desire tooth positioning via both sequential and contemporaneous movements of two or more teeth in up to three planes. For example, adjacent central teeth may be first spread and/or tipped to a first degree sufficient to permit subsequent contemporaneous rotation into position. Similarly, central and cuspids may be first spread and/or tipped to a degree sufficient for subsequent contemporaneous extrusion and/or root translation of a lateral therebetween. Analogous like movements can be achieved for positioning of the cuspids between first and second bicuspids.

Figure 3:
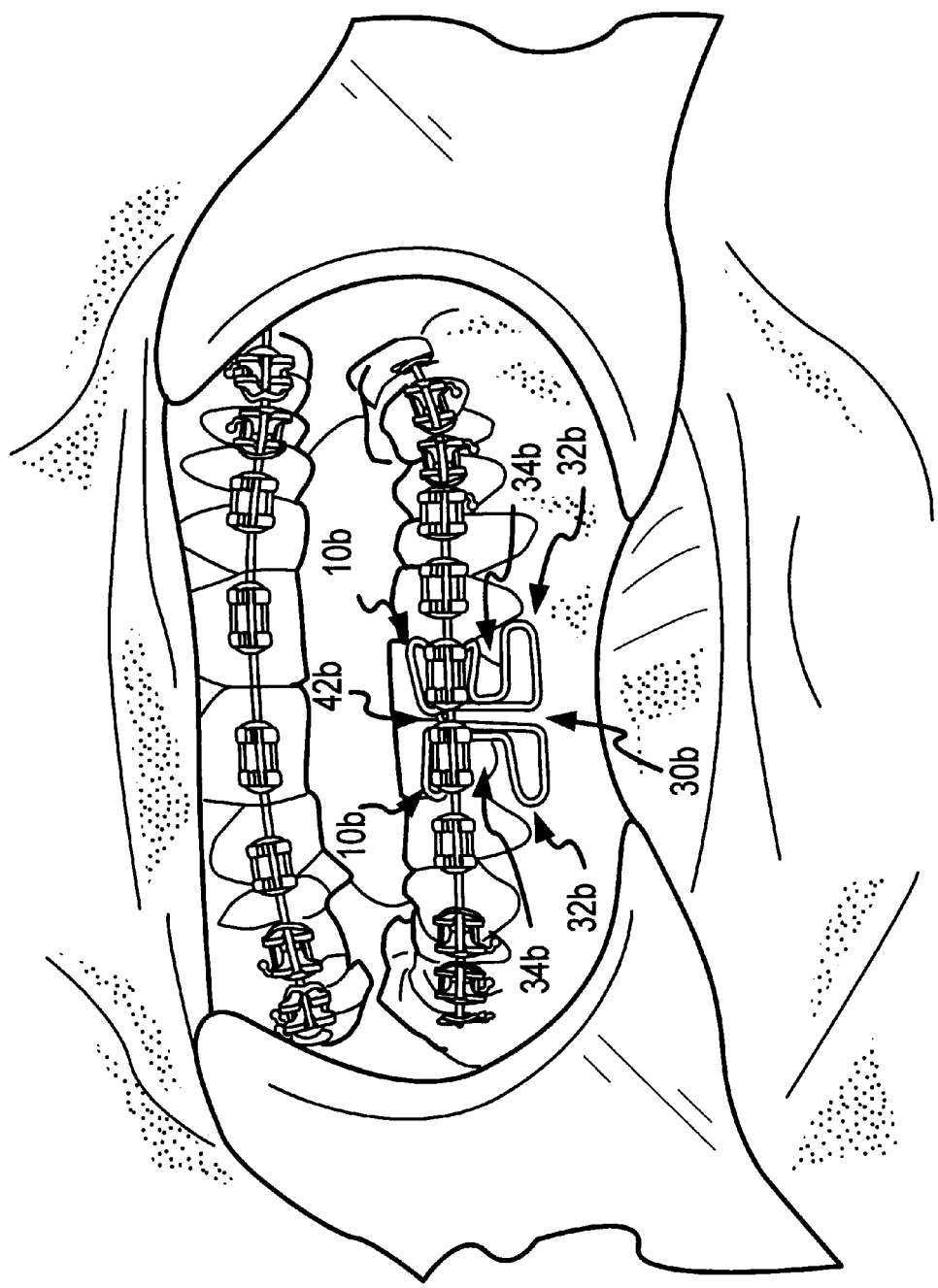
FIG. 3 illustrates an application of the orthodontic spring of FIGS. 1B and 2B.

FIG. 3 shows the orthodontic spring device 30b, illustrated in FIGS. 1b and 2b, mounted for use on a patient. More particularly, the orthodontic spring device 30b is mounted on the right and left central teeth in the mandibular jaw of a patient for interaction with a conventional fixed appliance system. More particularly, the conventional fixed appliance system includes edgewise brackets mounted on each of the teeth from right bicuspid to left bicuspid, buccal tubes mounted on each of the second bicuspids, a round archwire passing between the buccal tubes and edgewise brackets. Ligatures are positioned over the gingivally-extending and occlusally-extending tie wings of each bracket as well as the rounded archwire passing through the mesial-distal slot in each bracket. As illustrated, the attachment ends 10b of the orthodontic spring device 30b are positioned in gripping, outward-facing engagement with an edgewise bracket on each of the lower right and left central teeth. More particularly, each attachment end 10b is positioned to interface with the gingival and occlusal sides of an edgewise bracket, as well as a mesial bracket side in the application shown in FIG. 3. Each attachment end 10b is positioned lingually relative to the tie wings and interfacing ligature and can actively interface with the lingual-facing, or underneath, surface of each tie wing to facilitate tooth rotation as necessary. Spring segment 42b is positioned lingually relative to the orthodontic archwire and can interact therewith during use. Further, it is noted that foot spring segments 32b are disposed so that they will avoid engagement with the gums of the patient. In the arrangement of FIG. 3, orthodontic spring device 30b will serve, inter alia, to open space between the lower centrals.

Figure 4:
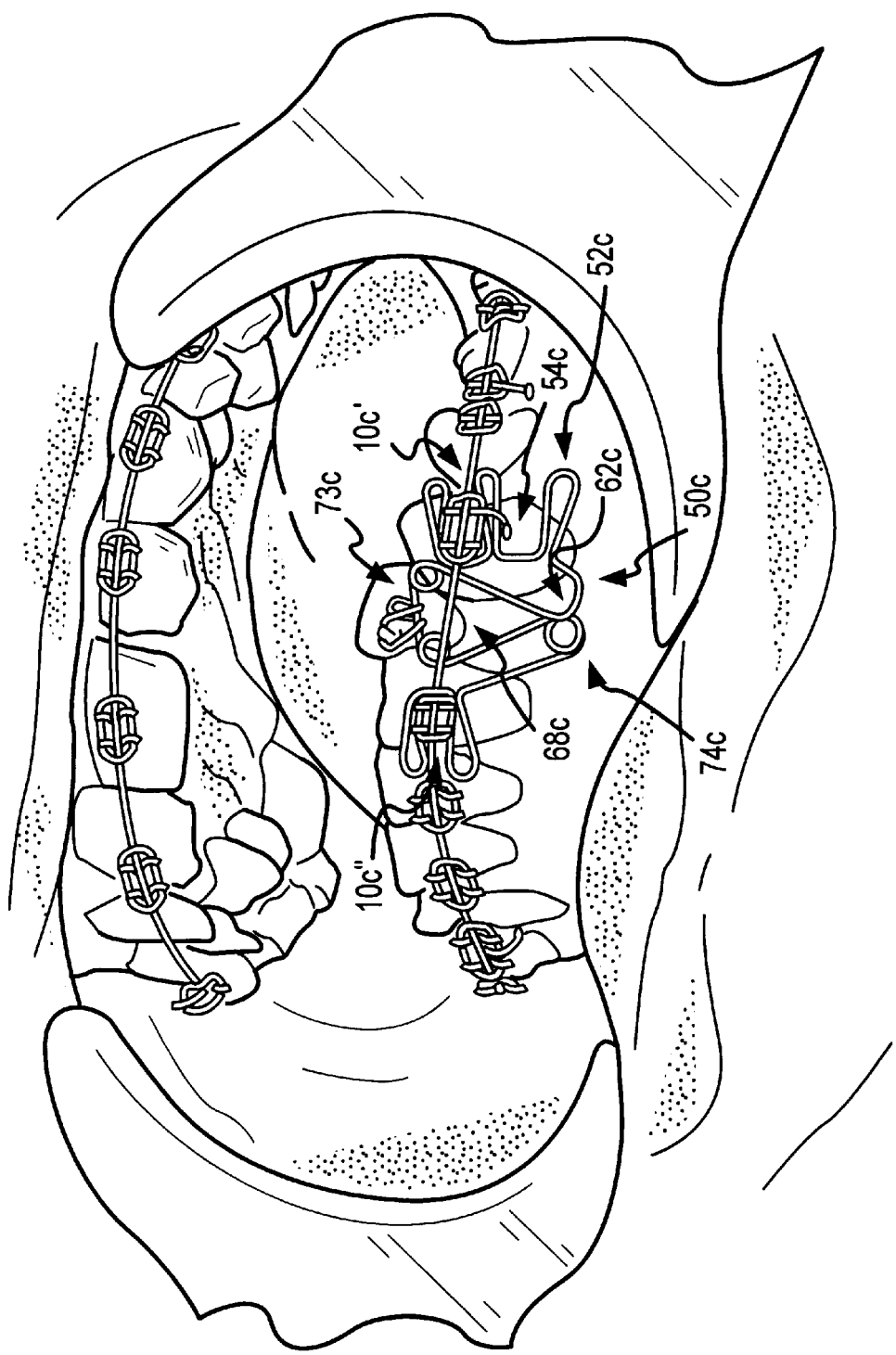
FIG. 4 illustrates an application of the orthodontic spring of FIGS. 1C and 2C.

FIG. 4 illustrates the orthodontic device 50c illustrated in FIGS. 1C and 2C, mounted for use on a patient. In this application, the orthodontic spring device 50c is interconnected to the right lateral, cuspid and first bicuspid teeth in the maxillary jaw of the patient. The conventional fixed appliance system includes standard edgewise brackets mounted on each of the teeth from the right second bicuspid to the left second bicuspid. A round archwire is positioned between the mesial-distal slots of the edgewise brackets and a ligature is utilized on each bracket to interface the bracket with the archwire. As illustrated, the attachment end 10c' is positioned in gripping engagement with the bracket located on the upper right first bicuspid and the attachment end 10c" is mounted for gripping engagement with the edgewise bracket mounted on the upper right lateral tooth. More particularly, each attachment end 10c' and 10c" is positioned to interface with the gingival and occlusal facing sides of their corresponding edgewise brackets, as well as the mesial side of the bracket on the upper first bicuspid and distal side of the bracket on the upper right lateral, respectively. In the application of the orthodontic spring device 50c shown in FIG. 4, spring segment 68c and 74c are each activated to provide tooth spreading forces to provide room for the cuspid tooth. In the latter regard, the bracket on the upper right cuspid tooth is interconnected via a ligature to the tie in segment 73c of the spring segment 68c, and the helical loop bends 70c, 72c, 74c, as well as other bends in the bracket, are activated so as to pull the upper right cuspid tooth forward. Further, spring segments 52c and 54c are activated for purposes of applying a gingivally directed tooth force for intruding the upper right cuspid tooth via the tie in segment 73c interconnected to the cuspid.

Figure 5:
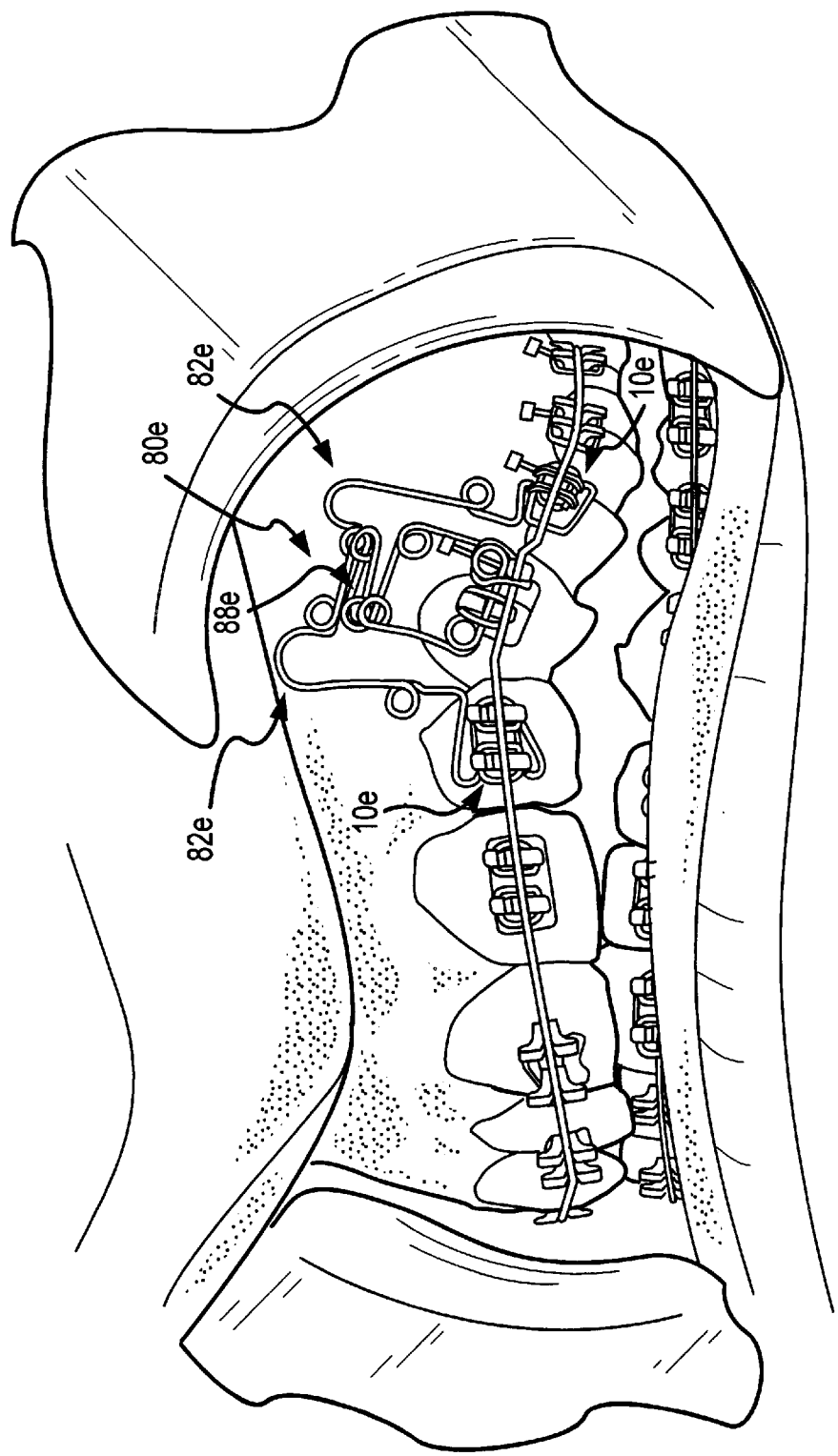
FIG. 5 illustrates an application of the orthodontic spring of FIGS. 1E- and 2E.

FIG. 5 illustrates orthodontic spring device 80e in use on a patient. In this application, the orthodontic spring device 80e is interconnected to the upper left cuspid, first bicuspid and second bicuspid of the patient. The conventional fixed appliance system includes standard edgewise brackets mounted on each of the teeth. A braided arch wire is positioned through the mesial-distal slots of the edgewise brackets on the cuspid and second bicuspids, and ligatures are utilized to interface the brackets with the arch wire. As illustrated, the attachment ends 10e are interconnected to the cuspid and second bicuspid teeth. Spring segments 82e have been activated to provide additional room for is first bicuspid therebetween. Further, spring segments 88e have been further activated for extruding the first bicuspid via ligation to tie-in side 98e.

Figure 6A:
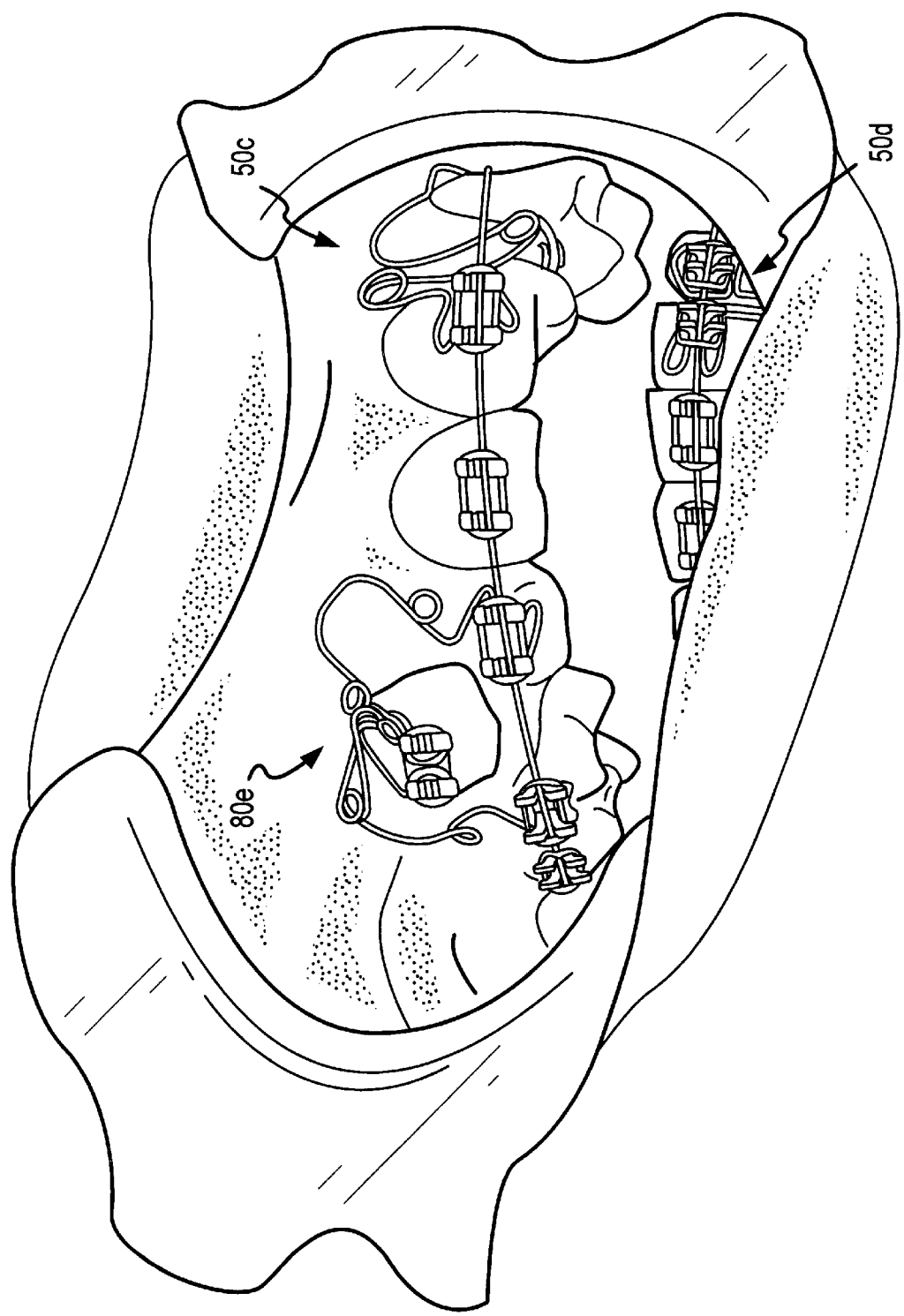
FIGS. 6A–6F illustrate the progression of teeth positioning in an exemplary application of the orthodontic spring devices of FIGS. 1C, 1D and 1E.
Figure 6B:
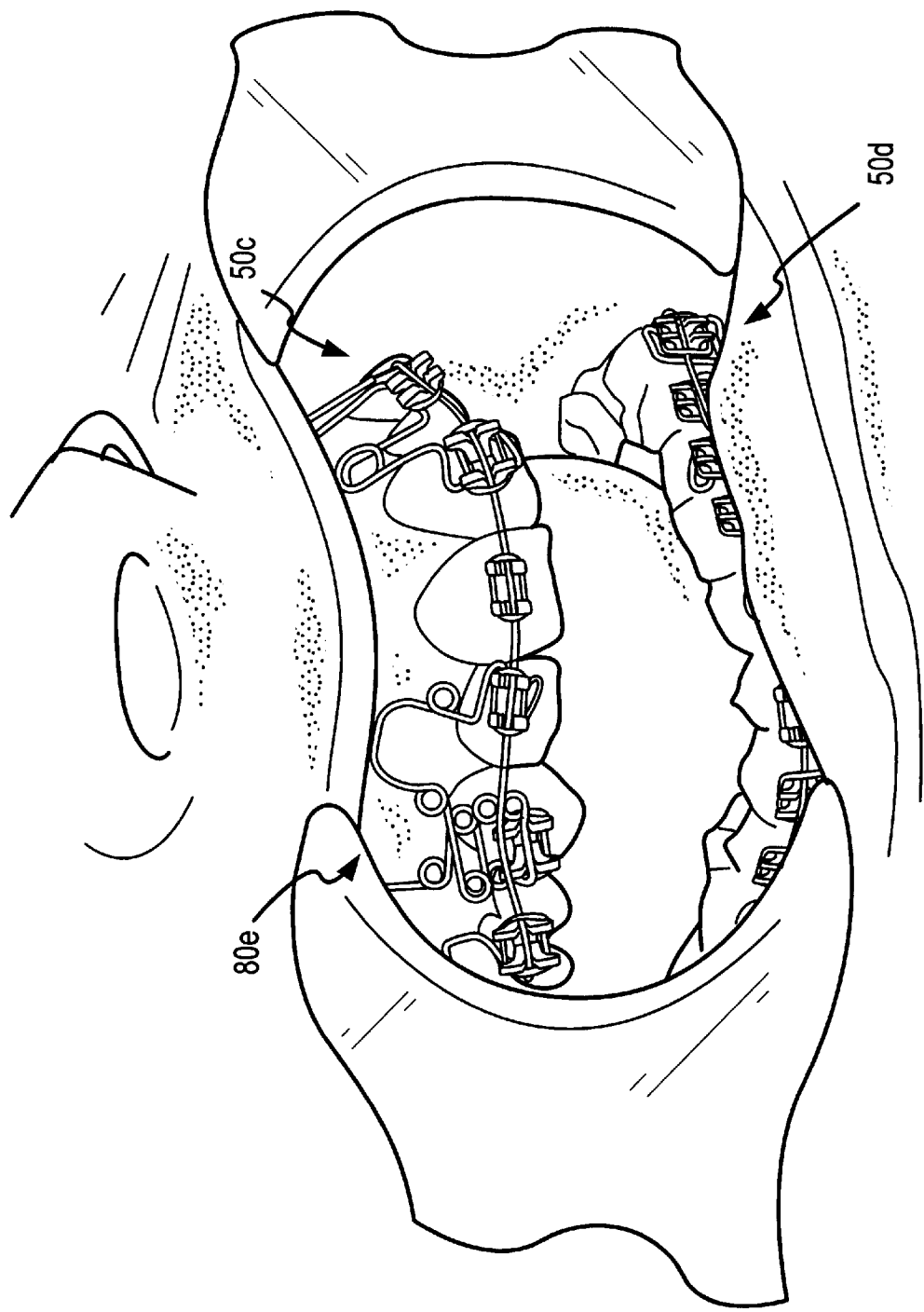
Figure 6C:
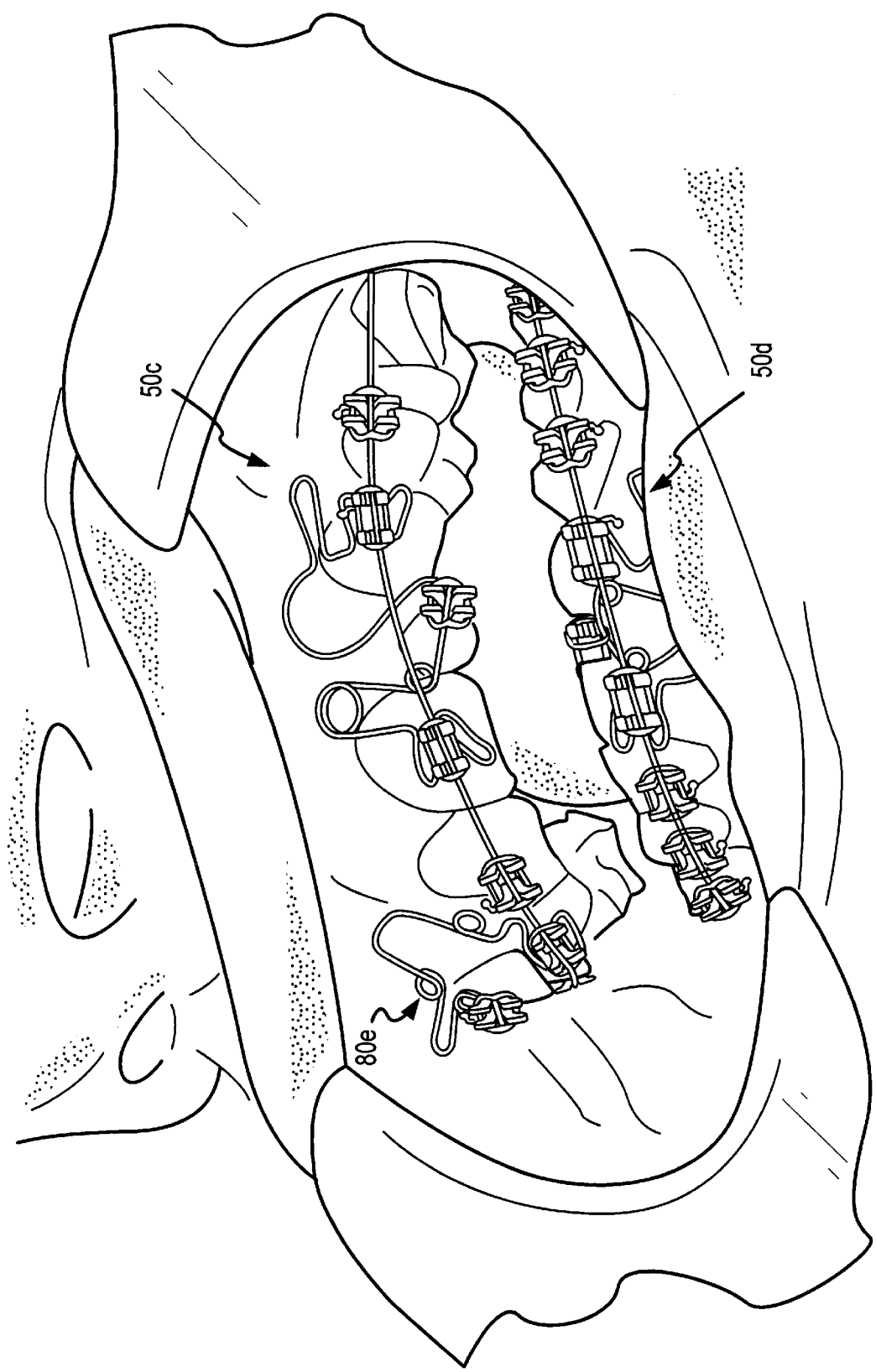
Figure 6D:
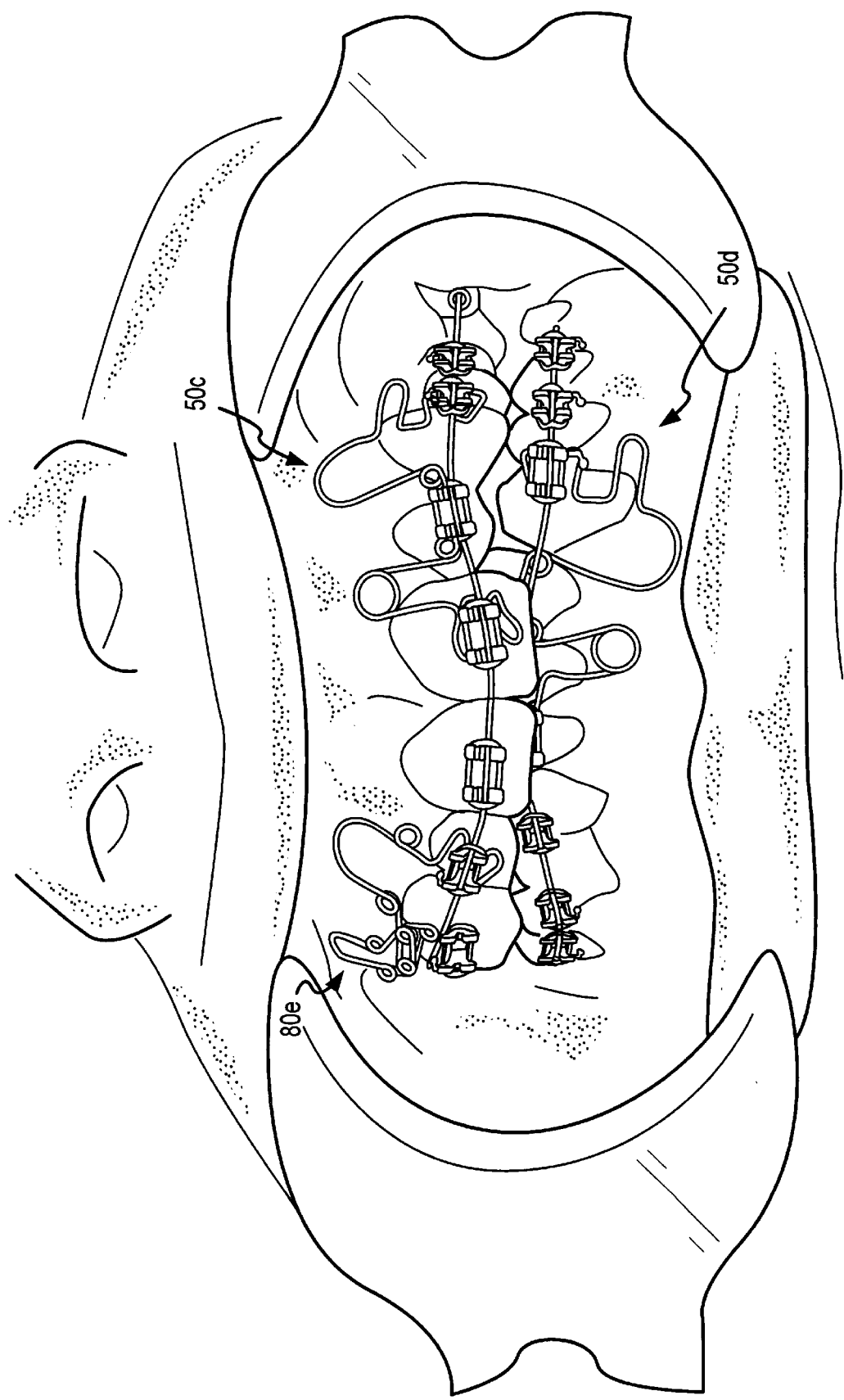
Figure 6E:
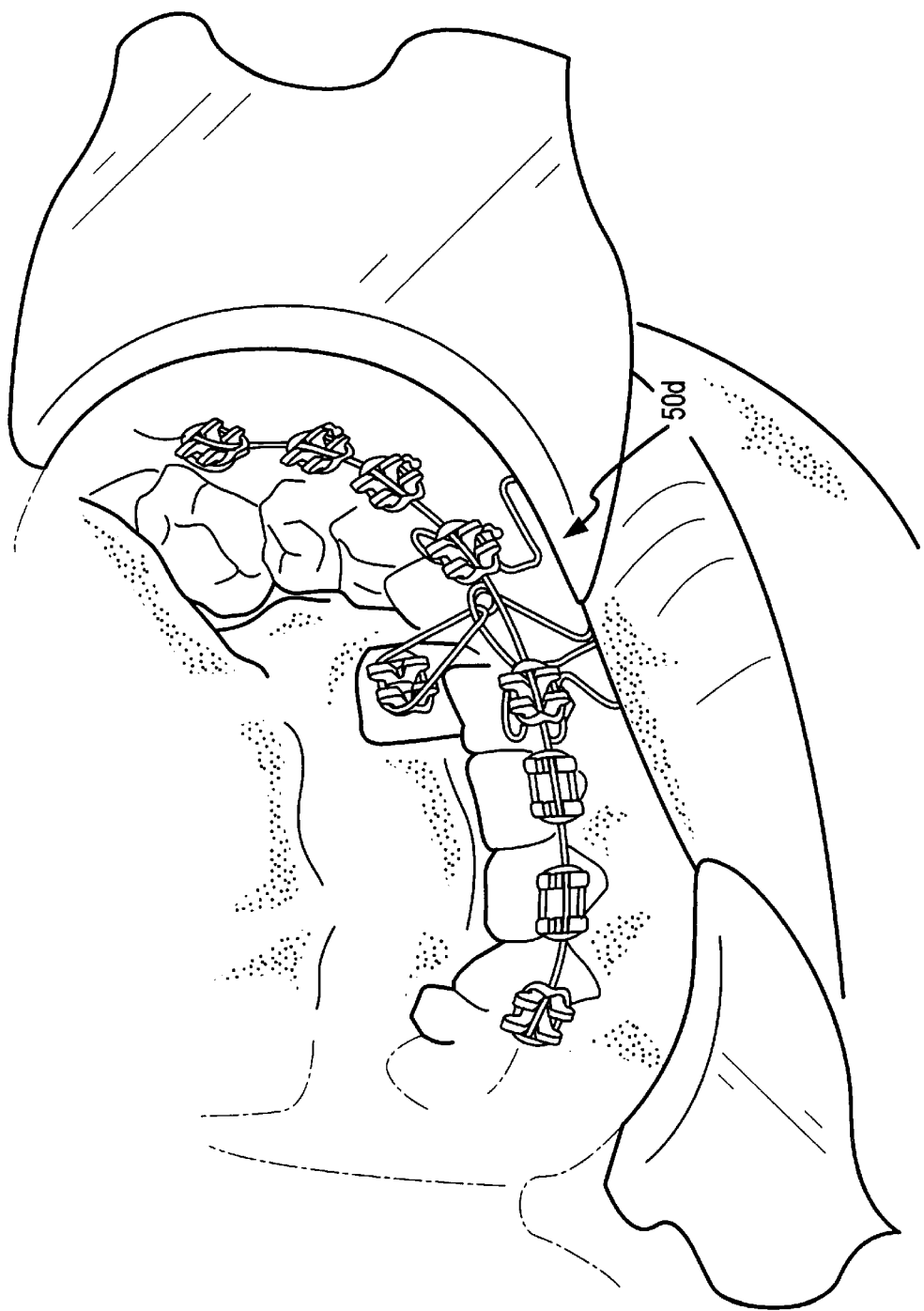
Figure 6F:
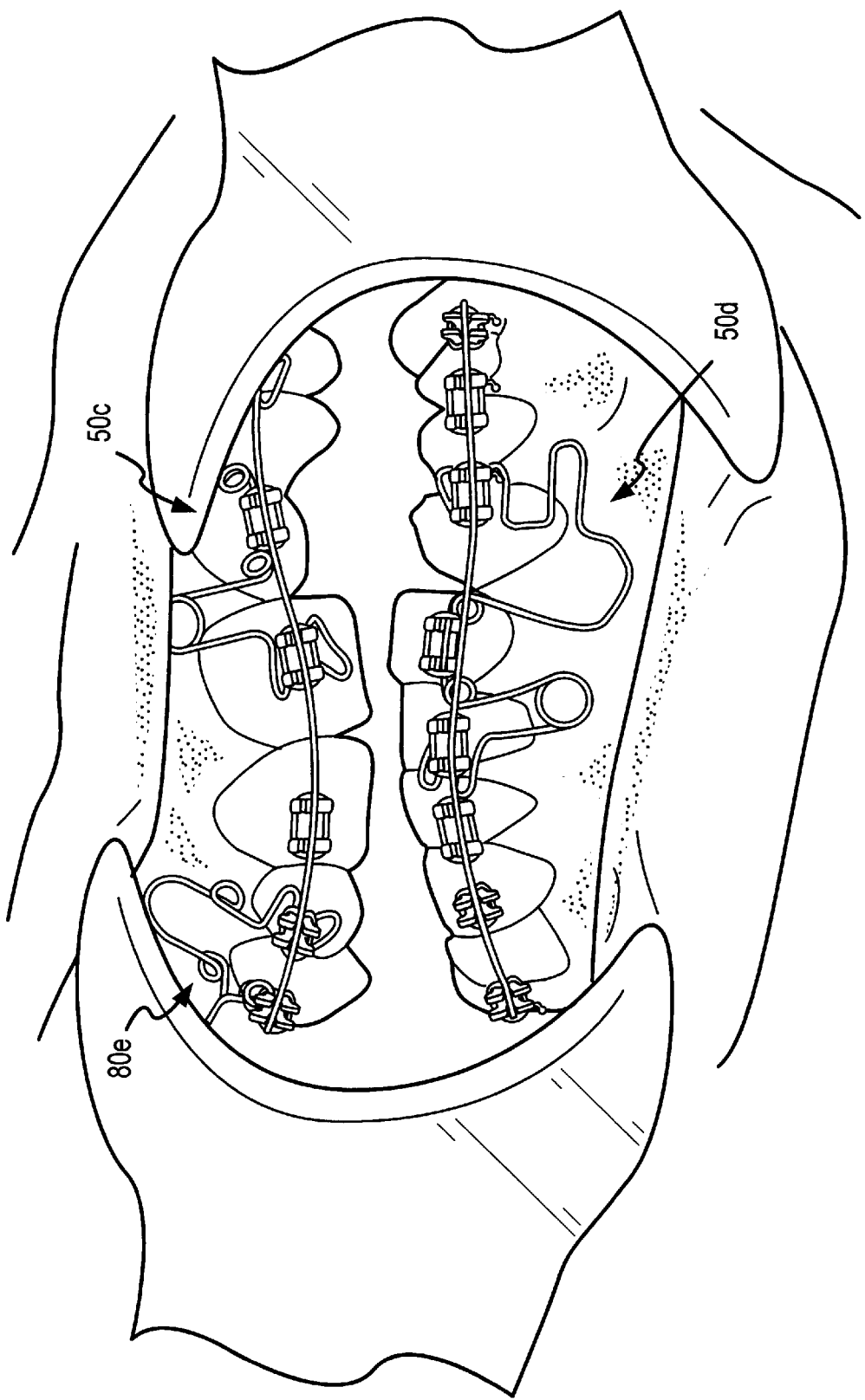

FIGS. 6A–6F illustrate the contemporaneous use of orthodontic spring devices 80e, 50c and 50d in different quadrants of a patient. More particularly, FIGS. 6A, 6C and 6E illustrate the position of spring devices 80e, 50c and 50d and interconnected teeth at the outset of the treatment, and FIGS. 6B, 6D and 6F illustrate the position of such spring devices and interconnected teeth after just three months of treatment. The maxillary right cuspid was initially about 4.5 mm "high" (i.e., vertically off the occlusal plane), and the cuspid was also out of the arch form to the labial approximately 4.5 mm. Additionally, the axis of the maxillary right cuspid was slightly root distal. As illustrated, in FIGS. 6A, 6B, the spring device 80e was installed in a highly activated state, and as the upper right cuspid was extruded, brought into the arch form and the root translated slightly mesially, spring device 80e approached a passive state. In FIGS. 6C and 6D, orthodontic spring device 50c was utilized to rotate the upper left lateral and translate the root slight distally. As shown in FIGS. 6E and 6F, spring device 50d was utilized to spread the lower left central and cuspid teeth, and to rotate and advance (i.e., via root translation) the lower left lateral therebetween. At the same time, via interaction across the lower arch, the arch was reformed with the lower right cuspid and lower right lateral being rotated.

Figure 7A:
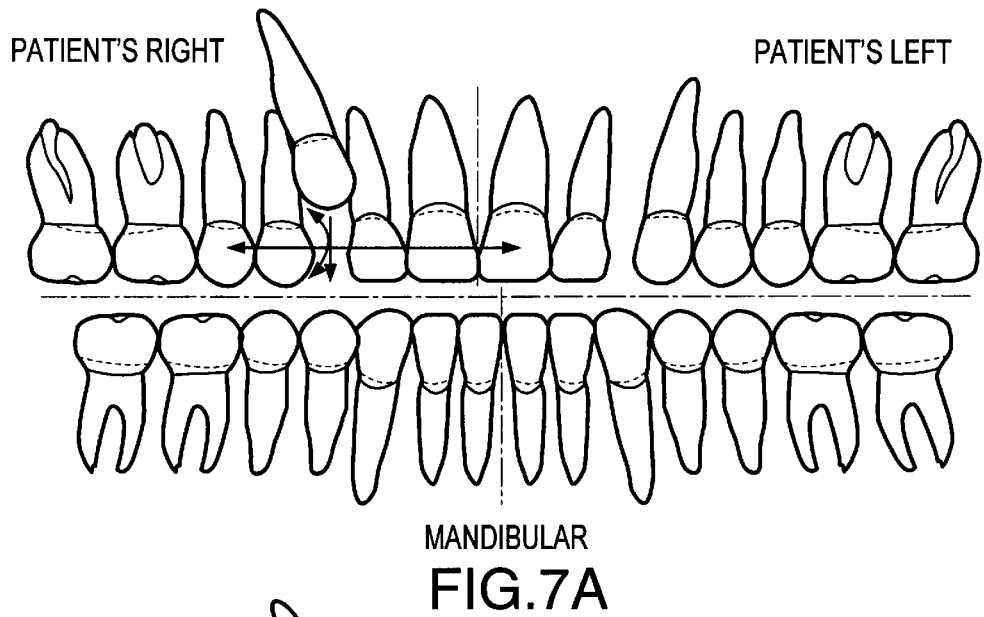
FIGS. 7A–7C schematically illustrate the tooth repositioning shown in FIGS. 6A and 6B.
Figure 7B:
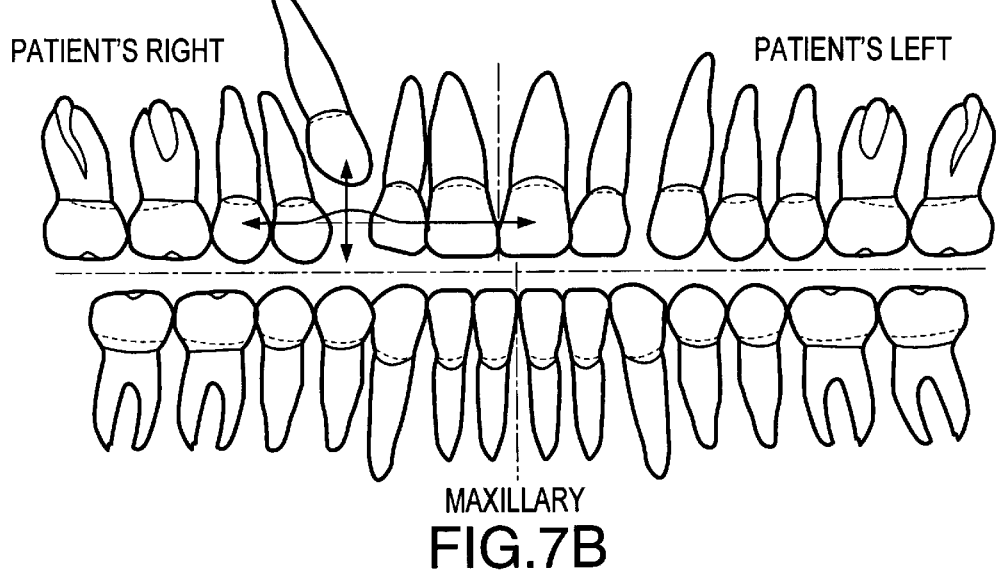
Figure 7C:
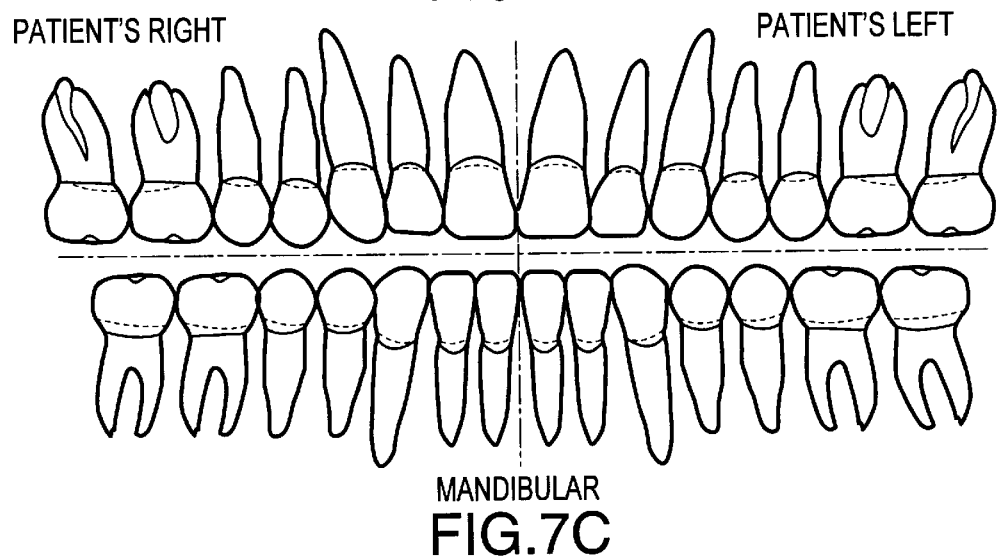

As shown in FIGS. 7A–7C, the movement of teeth, corresponding with FIGS. 6A and 6B is achieved through effective tooth and root movement, wherein the roots of adjacent teeth achieve a significant degree of parallel orientation. This is in contrast to prior art techniques in which adjacent teeth movements are primarily achieved via tipping teeth alternately in mesial, then distal, then mesial, etc., directions, thereby resulting in and even causing non-parallel root positioning.

Numerous additional usages of the spring devices and invention disclosed herein are possible. For example, and while not illustrated, two of the disclosed orthodontic spring devices can be interconnected to a "loose" bracket at one of each of their attachment ends so as to cooperatively bridge and close wide expanses. Additional variations will be apparent to those skilled in the art and are intended to be within the scope of the present invention as contemplated by the claims which follow.

What is claimed is:

1. An orthodontic device for selected interconnection to at least one orthodontic appliance comprising a fixed orthodontic appliance system, including:
   at least one U-shaped attachment end for selective attachment to said at least one orthodontic appliance;
   said at least one U-shaped attachment end including:
      a first spring leg;
      a second spring leg positioned in opposing relation to the first spring leg,
   wherein said device is formed from a length of bent wire and at least one of said first and second spring legs comprises a looped portion of said wire to define a key-hole shaped opening between the first and second spring legs for receiving said at least one orthodontic appliance therethrough, and wherein said at least one U-shaped attachment end actively grips a portion of said at least one orthodontic appliance between said first and second spring legs during use.

2. A device as recited in claim 1, wherein said first spring leg and second spring leg are spaced by at least a first distance in an inactive state, and wherein said first distance is less than a cross sectional width of said portion of said orthodontic appliance.

3. Device as recited in claim 2, wherein said first and second spring legs are spring-loaded to provide active gripping forces upon activation.

4. A device as recited in claim 1, further comprising:
   a second U-shaped attachment end for selective attachment to a second orthodontic appliance comprising said fixed orthodontic appliance system;

said second U-shaped attachment end including:
   a first spring leg;
   a second spring leg positioned in opposing relation to the first spring leg of said second U-shaped attachment end, wherein said second U-shaped attachment end actively grips a portion of said second orthodontic appliance between said first and second spring legs thereof during use.

5. A device as recited in claim 4, further comprising:
   at least one spring segment positioned between said first and second U-shaped attachment ends and activatable to apply a tooth aligning force in a first direction.

6. Device as recited in claim 5, wherein said device is formed from a length of bent wire, and further comprising:
   at least one bend interposed between said at least one U-shaped attachment end and said at least one spring segment, wherein said at least one U-shaped attachment end is deflectable about said bend.

7. A device as recited in claim 5, wherein said at least one spring segment is U-shaped to define a U-shaped opening for receiving frenum tissue during use.

8. A device as recited in claim 5 wherein said at least one U-shaped attachment end has a first center axis in an inactive state, wherein said at least one spring segment has a second center axis in an inactive state, and wherein said first and second center axes are oriented substantially perpendicular in said inactive state.

9. A device as recited in claim 5, further comprising:
   at least a second spring segment positioned between said first and second U-shaped attachment ends, wherein said at least one spring segment and said second spring segment have corresponding center axes which are substantially parallel.

10. A device as recited in claim 9, further comprising:
    an intermediate segment interposed between first and second spring segments.

11. Device as recited in claim 1, wherein said first and second spring legs are adapted to grippingly engage gingival-facing and occlusal-facing surfaces, respectively, of said at least one orthodontic appliance.

12. Device as recited in claim 11, said at least one U-shaped attachment end further comprising:
    a back interposed between said first and second spring legs, wherein said back is adapted to engage one of a mesial-facing and a distal-facing surface of said at least one orthodontic appliance.

13. Device as recited in claim 1, wherein said looped portion further defines a rounded end to facilitate engagement of said at least one U-shaped attachment end with said at least one orthodontic appliance.

14. An orthodontic device for selective interconnection to at least two orthodontic appliances, comprising:
    first and second U-shaped ends for selective attachment to first and second orthodontic appliances, respectively, each of said first and second U-shaped ends including:
       a first spring leg;
       a second spring leg position in opposing relation to the first spring leg;
    wherein said first U-shaped end actively grips a portion of the first orthodontic appliance during use;
    a first spring segment position between said first and second U-shaped attachment ends and activatable to apply a tooth aligning force in a first direction; and
    a second spring segment positioned between said first and second U-shaped ends and activatable to apply a second tooth aligning force in a second direction, said second direction being transverse to said first direction.

15. A device as recited in claim 14, further comprising:
    at least a third spring segment positioned between such said first and second U-shaped attachment ends and activatable to apply a third tooth aligning force in a third direction, said third direction being transverse to said first and second directions.

16. A device as recited in claim 14, wherein said at least one spring segment is of a U-shaped configuration having a first central axis in an inactive state, and wherein said second spring segment is of a U-shaped configuration having a second central axis in an inactive state; said first and second central axes being transverse in an inactive state.

17. A device as recited in claim 14, wherein said device is formed from a single length of bent wire, and wherein said orthodontic device lies substantially entirely within a single plane in an inactive state.

18. A device as recited in claim 17, further comprising:
    at least one bend interposed between said at least one and said second spring segments, wherein said device may deflect about said at least one bend during use.

19. A device as recited in claim 18, wherein said bend is defined by at least one of a 90° turn, a 180° turn and helical loop.

20. A device as recited in claim 14, wherein said at least one U-shaped attachment end has a center axis in an inactive state, said center axis being substantially parallel to a central axis of said at least one spring segment in an inactive state, and said center axis being substantially perpendicular to a central axis of said second spring segment in an inactive state.

21. A device as recited in claim 14, wherein said first direction is one of a mesial direction and distal direction, and wherein said second direction is one of a gingival direction and occlusal direction.

22. A device as recited in claim 14, wherein each of said spring segments has a corresponding substantially linear spring rate upon activation.

23. A device as recited in claim 14, wherein said at least one spring segment includes at least one helical loop.

24. A method to augment the positioning of one or more maloccluded teeth, relative to a plurality of teeth, said plurality of teed each having a corresponding orthodontic appliance interconnected thereto and being interconnected to an orthodontic arch wire, comprising:
    first interconnecting one end of an orthodontic spring to a first orthodontic appliance interconnected to a labial side of a first of said plurality of teeth, wherein a first attachment end of the orthodontic spring is positioned in substantially fixed relation to the first orthodontic appliance;
    second interconnecting another end of said orthodontic spring to a second orthodontic appliance interconnected to a labial side of a second of said plurality of teeth, wherein a second attachment end of the orthodontic spring is positioned in substantially fixed relation to the second orthodontic appliance;
    activating, contemporaneous with said second interconnecting step, said orthodontic spring to apply a force to at least one of said maloccluded teeth;
    utilizing said force to move at least one of said maloccluded teeth from a maloccluded position to a desired position, wherein in said desired position said orthodontic spring automatically assumes a substantially inactive state.

25. A method as recited in claim 24, wherein said activating step includes:

applying said force to said one or more of said maloccluded teeth in at least two different planes.

26. A method as recited in claim 25, wherein said two different planes are defined by two of the following orientations: mesial-distal, gingival-occlusal, a interior-posterior.

27. A method as recited in claim 24, wherein said activating step includes:

applying said force to said one or more maloccluded teeth in at least three different planes.

28. A method as recited in claim 24, wherein said first and second teeth are substantially adjacent.

29. A method as recited in claim 24, wherein a third tooth is positioned between said first and second teeth when said one or more maloccluded are moved into their corresponding desired positions.

30. A method as recited in claim 29, further comprising:

third interconnecting an intermediate portion of the orthodontic spring to said third tooth.

31. A method as recited in claim 30, further comprising:

fourth interconnecting said arch wire to a third orthodontic appliance interconnected to said third tooth.

32. A method as recited in claim 24, wherein:

said first interconnecting step includes gripping a portion of said first orthodontic appliance between opposing legs of the first attachment end of said orthodontic spring, said first attachment end being U-shaped; and said second interconnecting step includes gripping a portion of said second orthodontic appliance between opposing legs of the second attachment end, said second attachment end being U-shaped.

33. A method as recited in claim 32, wherein said first orthodontic appliance includes at least one tie wing, said utilizing step including:

engaging one of said opposing legs of the attachment end with a lingual surface of said tie wing.

34. A method as recited in claim 32, said activating step including:

activating a first segment of said orthodontic spring to apply a first positioning force in a first direction, wherein the first segment is located between the first and second attachment ends of the orthodontic spring; and activating a second segment of said orthodontic spring to apply a second positioning force in a second direction, said first and second directions being transverse, wherein the second segment is located between the first and second attachment ends of be orthodontic spring.

35. A method as recited in claim 34, wherein said first segment is defined by a first U-shaped bent wire portion and said second segment is defined by a second U-shaped bent wire portion.

36. A method as recited in claim 34, wherein said force is selectively employed for at least one of the following: tooth intrusion, tooth extrusion, mesial-distal teeth spacing, tooth tipping, tooth torquing, tooth long axis translation, and tooth rotation.

37. A method as recited in claim 32, wherein said first U-shaped attachment end is adjoined to an adjacent portion of said orthodontic spring by a bent wire section and further including:

deflecting said U-shaped attachment end about said first bend, wherein said U-shaped attachment end and said adjacent portion of said orthodontic spring lie in adjoining, transverse planes.

38. A method as recited in claim 24, wherein in said substantially inactive state said force is less than about 20 gms./mm.

39. A method as recited in claim 24, wherein at least a portion of said force is communicated to another of said maloccluded teeth via said arch wire.

40. A method as recited in claim 24, wherein at least a portion of said force is communicated to another of said maloccluded teeth via direct contact by said at least one of said maloccluded teeth.

* * * * *

UNITED STATES PATENT AND TRADEMARK OFFICE
CERTIFICATE OF CORRECTION

PATENT NO. : 5,984,675
DATED : November 16, 1999
INVENTOR(S) : WHITE, Velton Curtis It is certified that error appears in the above-identified patent and that said Letters Patent is hereby corrected as shown below:

Claim 6, Column 13, line 13, please insert "A" before the word "device";
Claim 11, Column 13, line 37, please insert "A" before the word "device";
Claim 12, Column 13, line 41, please insert "A" before the word "device";
Claim 13, Column 13, line 47, please insert "A" before the word "device";
Claim 14, Column 13, line 57, after "leg;" please insert "and,";
Claim 14, Column 13, line 58, please amend "position" to read "positioned".

Claim 15, Column 14, line 2, the word "such" has been deleted;
Claim 18, Column 14, line 20, after the words "during use", insert the words --so that adjacent portions of said first and second spring segments are positioned in transverse, adjoining planes--;
Claim 24, Column 14, line 42, the word "teed" has been amended to read --teeth--;
Claim 29, Column 15, line 14, after the word "maloccluded", insert the word --teeth--.

Signed and Sealed this

Twenty-fourth Day of October, 2000

Attest:

Q. TODD DICKINSON

*Attesting Officer*    *Director of Patents and Trademarks*